United States Patent [19]
Kimura et al.

[11] Patent Number: 5,846,790
[45] Date of Patent: Dec. 8, 1998

[54] METHODS OF PRODUCING L-LYSINE AND L-GLUTAMIC ACID BY FERMENTATION

[75] Inventors: Eiichiro Kimura; Yoko Asakura; Akinori Uehara; Sumio Inoue; Yoshio Kawahara; Yasuhiko Yoshihara; Tsuyoshi Nakamatsu, all of Kawasaki, Japan

[73] Assignee: Ajinomoto Co., Inc., Tokyo, Japan

[21] Appl. No.: 776,597

[22] PCT Filed: Aug. 9, 1995

[86] PCT No.: PCT/JP95/01586

§ 371 Date: Feb. 18, 1997

§ 102(e) Date: Feb. 18, 1997

[87] PCT Pub. No.: WO96/06180

PCT Pub. Date: Feb. 29, 1996

[30] Foreign Application Priority Data

Aug. 19, 1994 [JP] Japan ................................. 6-195465

[51] Int. Cl.⁶ .......................... C12P 13/08; C12P 13/14; C12P 1/21; C12P 15/09
[52] U.S. Cl. ......................... 435/110; 435/111; 435/115; 435/252.1; 435/252.32; 435/840; 435/843
[58] Field of Search .................... 435/252.1, 110, 435/111, 115, 840, 843, 252.32

[56] References Cited

U.S. PATENT DOCUMENTS

| | | | |
|---|---|---|---|
| 3,971,701 | 7/1976 | Takinami et al. | 435/111 |
| 4,334,020 | 6/1982 | Nakazawa et al. | 435/110 |

*Primary Examiner*—Herbert J. Lilling
*Attorney, Agent, or Firm*—Oblon, Spivak, McClelland, Maier & Neustadt, P.C.

[57] ABSTRACT

A mutant strain having an ability to produce L-glutamic acid in the absence of any biotin action-suppressing agent in a medium containing an excessive amount of biotin is obtained by giving temperature sensitivity with respect to a biotin action-suppressing agent to a coryneform L-glutamic acid-producing bacterium. This strain is cultivated in a liquid medium to produce and accumulate L-glutamic acid in the medium. A mutant strain having an ability to produce L-lysine and L-glutamic acid in the absence of any biotin action-suppressing agent in a medium containing an excessive amount of biotin is obtained by giving temperature sensitivity with respect to a biotin action-suppressing agent and giving L-lysine productivity to a coryneform L-glutamic acid-producing bacterium. This strain is cultivated in a liquid medium to simultaneously produce and accumulate L-lysine and L-glutamic acid in the medium.

15 Claims, 3 Drawing Sheets

—○— growth of ATCC13869 at 31.5°C
—●— growth of ATCC13869 at 35.0°C
—△— growth of AJ13029 at 31.5°C
—▲— growth of AJ13029 at 35.0°C

METHODS OF PRODUCING L-LYSINE AND L-GLUTAMIC ACID BY FERMENTATION

TECHNICAL FIELD

The present invention relates to methods of producing L-lysine and L-glutamic acid by fermentation. L-lysine is widely used as a feed additive, etc., and L-glutamic acid is widely used as a material for seasonings, etc.

BACKGROUND ART

L-lysine and L-glutamic acid have been hitherto industrially produced by fermentatative methods by using coryneform bacteria belonging to the genus Brevibacterium or Corynebacterium having abilities to produce these amino acids. In these methods, it is known that the coryneform bacteria require biotin for their growth, while L-glutamic acid is not accumulated if an excessive amount of biotin exists in a medium. Therefore, any one of the following methods has been adopted in the conventional method of producing L-glutamic acid. Namely, cultivation is conducted in a medium in which the concentration of biotin is restricted, or cultivation is conducted such that a surfactant or a lactam antibiotic as a biotin action-suppressing agent is allowed to be contained in a medium at an initial or intermediate stage of cultivation in the case of use of the medium containing a sufficient amount of biotin.

However, especially when a material such as waste molasses, which is inexpensive but contains an excessive amount of biotin, is used as a carbon source in a medium, the biotin action-suppressing agent, which is required to be added to the medium, has been a cause to increase the production cost.

On the other hand, the following methods are known for simultaneous production of L-lysine and L-glutamic acid by fermentation. Namely, an L-lysine-producing bacterium is cultivated under a condition for L-glutamic acid production, or an L-lysine-producing bacterium and an L-glutamic acid-producing bacterium are mixed and cultivated (Japanese Patent Laid-open No. 5-3793).

However, in the method in which an L-lysine-producing bacterium is cultivated under a condition for L-glutamic acid production to simultaneously produce L-lysine and L-glutamic acid by fermentation, the condition for L-glutamic acid production is either that a biotin-auxotrophic bacterium belonging to the genus Brevibacterium or Corynebacterium is cultivated in a medium containing a low concentration of biotin, or that it is cultivated such that a surfactant or a lactam antibiotic is allowed to be contained in a medium at an initial or intermediate stage of cultivation in the case of the medium containing a sufficient amount of biotin. Especially when a material such as waste molasses, which is inexpensive but contains an excessive amount of biotin, is used as a carbon source in a medium, the surfactant or the lactam antibiotic as a biotin action-suppressing agent to be added to the medium has been a cause to increase the production cost.

Further, in the method in which an L-lysine-producing bacterium and an L-glutamic acid-producing bacterium are mixed and cultivated, there has been a problem that control of cultivation is difficult, and fermentation results are unstable.

DISCLOSURE OF THE INVENTION

An object of the present invention is to provide a method of producing L-glutamic acid inexpensively and stably by fermentation in which no biotin action-suppressing agent is added even when a material such as waste molasses containing an excessive amount of biotin is used as a carbon source in a medium.

Another object of the present invention is to provide a method of simultaneously producing L-lysine and L-glutamic acid inexpensively and stably by fermentation in which no biotin action-suppressing agent is added even when a material such as waste molasses containing an excessive amount of biotin is used as a carbon source in a medium.

As a result of vigorous investigations in order to achieve the aforementioned objects, the present inventors have found that a mutant strain obtained by giving temperature sensitivity to a biotin action-suppressing agent to a conventionally used coryneform L-glutamic acid-producing bacterium produces and accumulates a considerable amount of L-glutamic acid even in a medium containing an excessive amount of biotin without adding any surfactant or antibiotic. Further, the present inventors have found that a mutant strain derived by giving temperature-sensitivity to a biotin action-suppressing agent to an L-lysine-producing bacterium originating from a coryneform L-glutamic acid-producing bacterium produces and accumulates considerable amounts of both L-lysine and L-glutamic acid even in a medium containing an excessive amount of biotin without containing any surfactant or antibiotic. Thus the present invention has been completed.

Namely, the present invention lies in a method of producing L-glutamic acid by fermentation comprising the steps of cultivating a mutant strain in a liquid medium, producing and accumulating L-glutamic acid in the medium, and collecting it from the medium, the mutant strain originating from a coryneform L-glutamic acid-producing bacterium, having temperature sensitive mutation to a biotin action-suppressing agent, and having an ability to produce L-glutamic acid in the absence of any biotin action-suppressing agent in any medium containing an excessive amount of biotin.

In another aspect, the present invention lies in a method of producing L-lysine and L-glutamic acid by fermentation comprising the steps of cultivating a mutant strain in a liquid medium, producing and accumulating L-lysine and L-glutamic acid in the medium, and collecting them from the medium, the mutant strain originating from a coryneform L-glutamic acid-producing bacterium, having mutation to give L-lysine productivity and temperature sensitive mutation to a biotin action-suppressing agent, and having an ability to produce L-lysine and L-glutamic acid in the absence of any biotin action-suppressing agent in any medium containing an excessive amount of biotin.

According to another aspect of the present invention, there is provided a mutant strain originating from a coryneform L-glutamic acid-producing bacterium, having temperature sensitive mutation to a biotin action-suppressing agent, and having an ability to produce L-glutamic acid in the absence of any biotin action-suppressing agent in a medium containing an excessive amount of biotin. This mutant strain will be sometimes referred to below as "first mutant strain of the present invention".

According to another aspect of the present invention, there is provided a mutant strain originating from a coryneform L-glutamic acid-producing bacterium, having mutation to give L-lysine productivity and temperature sensitive mutation to a biotin action-suppressing agent, and having an ability to produce both L-lysine and L-glutamic acid in the absence of any biotin action-suppressing agent in a medium containing an excessive amount of biotin. This mutant strain will be sometimes referred to below as "second mutant strain of the present invention".

According to another aspect of the present invention, there is provided a method of breeding mutant strains having an ability to produce L-glutamic acid in the absence of any biotin action-suppressing agent in a medium containing an excessive amount of biotin comprising giving temperature sensitivity to a biotin action-suppressing agent to a coryneform L-glutamic acid-producing bacterium.

According to another aspect of the present invention, there is provided a method of breeding mutant strains having an ability to produce both L-lysine and L-glutamic acid in the absence of any biotin action-suppressing agent in a medium containing an excessive amount of biotin comprising giving temperature sensitivity to a biotin action-suppressing agent and L-lysine productivity to a coryneform L-glutamic acid-producing bacterium.

The present invention will be explained in detail below.

<1> PREPARATION OF MUTANT STRAIN TEMPERATURE-SENSITIVE TO BIOTIN ACTION-SUPPRESSING AGENT ORIGINATING FROM L-GLUTAMIC ACID-PRODUCING BACTERIUM, AND PRODUCTION OF L-GLUTAMIC ACID

[1] Preparation of Mutant Strain Temperature-Sensitive to Biotin Action-Suppressing Agent Originating from L-Glutamic Acid-Producing Bacterium Conventional and known L-glutamic acid-producing bacteria originating from coryneform L-glutamic acid-producing bacteria, when they are cultivated in a medium containing an excessive amount of biotin of not less than 10 μg/L, substantially produce no L-glutamic acid in a culture liquid, unless a biotin action-suppressing agent such as surfactants and antibiotics is allowed to be contained in the medium at an initial or intermediate stage of cultivation. The first mutant strain of the present invention has an ability to produce L-glutamic acid even when it is cultivated in a liquid medium containing an excessive amount of biotin, without allowing any biotin action-suppressing agent to be contained in the medium. Namely, the first mutant strain of the present invention is a mutant strain originating from a coryneform L-glutamic acid-producing bacterium, having temperature-sensitive mutation to a biotin action-suppressing agent, and having an ability to produce L-glutamic acid in the absence of any biotin action-suppressing agent in a medium containing an excessive amount of biotin.

The mutant strain as described above can be induced by giving temperature sensitivity to a biotin action-suppressing agent to a glutamic acid-producing bacterium originating from a coryneform L-glutamic acid-producing bacterium. The biotin action-suppressing agent includes, for example, surfactants and antibiotics.

The surfactants include, for example, saturated fatty acid such as lauric acid, myristic acid, stearic acid, and palmitic acid; fatty acid ester type nonionic surfactants such as glycerol fatty acid ester, sorbitan fatty acid ester, sucrose fatty acid ester, polyethylene glycol fatty acid ester, polyethylene glycol polypropylene glycol fatty acid ester, and polyoxyethylene sorbitan fatty acid ester; and N-acyl amino acids such as N-palmitoylglycine, N-palmitoylalanine, N-palmitoylvaline, N-palmitoylleucine, N-palmitoylthreonine, N-palmitoylmethionine, N-palmitoylaspartic acid, N-palmitoylglutamic acid, N-myristoylglutamic acid, N-stearoylglutamic acid, N,N'-dipalmitoylornithine, and N,N'-dipalmitoyllysine.

The antibiotics include, for example, lactam antibiotics such as penicillin and cephalolysine.

In general, the growth of coryneform L-glutamic acid-producing bacteria is inhibited by the presence of a biotin action-suppressing agent at a certain concentration or more. In the present invention, the temperature sensitivity to a biotin action-suppressing agent means a property such that growth is remarkably inhibited, as compared with that in the absence of the biotin action-suppressing agent, at a cultivation temperature of 33°–37° C., preferably not less than 34° C. in the presence of the biotin action-suppressing agent at a maximum concentration at which approximately equivalent growth to that in the absence of the biotin action-suppressing agent is observed at 31.5° C. (optimum growth temperature). Specifically, a property as defined as follows is intended. Namely, when the influence exerted by the biotin action-suppressing agent is investigated at temperatures of 31.5° C. and 33°–370° C., a degree of relative growth in the presence of the biotin action-suppressing agent at each concentration is calculated provided that each growth in the absence of the biotin action-suppressing agent at each temperature is regarded as 100, and a maximum concentration at which the degree of relative growth at 31.5° C. is not less than 80 is determined, then the degree of relative growth at a temperature of 33°–37° C. is not more than 50 in the presence of the biotin action-suppressing agent at the maximum concentration.

The coryneform L-glutamic acid-producing bacteria referred to in the present invention include bacteria having been hitherto classified into the genus Brevibacterium but united as bacteria belonging to the genus Corynebacterium at present (*Int. J. Syst. Bacteriol.*, 41, 255 (1981)), and include bacteria belonging to the genus Brevibacterium closely relative to the genus Corynebacterium. Therefore, the mutant strain used in the present invention can be induced from the following coryneform L-glutamic acid-producing bacteria belonging to the genus Brevibacterium or Corynebacterium. In this specification, when the L-glutamic acid productivity is not referred to, the bacteria belonging to the genera Corynebacterium and Brevibacterium are simply referred to as "coryneform bacteria".

| | |
|---|---|
| Corynebacterium acetoacidophilum | ATCC 13870 |
| Corynebacterium acetoglutamicum | ATCC 15806 |
| Corynebacterium callunae | ATCC 15991 |
| Corynebacterium glutamicum | ATCC 13032 |
| (Brevibacterium divaricatum) | ATCC 14020 |
| (Brevibacterium lactofermentum) | ATCC 13869 |
| (Corynebacterium lilium) | ATCC 15990 |
| (Brevibacterium flavum) | ATCC 14067 |
| Corynebacterium melassecola | ATCC 17965 |
| Brevibacterium saccharolyticum | ATCC 14066 |
| Brevibacterium immariophilum | ATCC 14068 |
| Brevibacterium roseum | ATCC 13825 |
| Brevibacterium thiogenitalis | ATCC 19240 |
| Microbacterium ammoniaphilum | ATCC 15354 |
| Corynebacterium thermoaminogenes | AJ12340 (FERM BP-1 539) |

The bacterial strain having temperature sensitivity to the biotin action-suppressing agent can be obtained by applying a mutation treatment such as ultraviolet light irradiation, X-ray irradiation, radiation irradiation, and mutating agent treatments to a bacterial strain as described above, followed by conducting a replica method on an agar plate medium containing the biotin action-suppressing agent. Namely, the growth state of a parent strain in the presence of several concentrations of the biotin action-suppressing agent is observed at a cultivation temperature of 33°–37° C., preferably not less than 34° C. to determine a maximum concentration of the biotin action-suppressing agent at which growth is recognized. A mutant strain may be separated which cannot grow or has a remarkably lowered growth speed in the presence of the biotin action-suppressing agent at the maximum concentration at the same temperature as that used above.

The temperature sensitivity to the biotin action-suppressing agent is given to the coryneform L-glutamic acid-producing bacterium as described above. Thus the mutant strain can be bred which has the ability to produce L-glutamic acid in the absence of the biotin action-suppressing agent in a medium containing an excessive amount of biotin.

[2] Preparation of Mutant Strain Temperature-Sensitive to Biotin Action-Suppressing Agent Originating from L-Glutamic Acid-Producing Bacterium by Means of Genetic Recombination Alternative methods for obtaining mutant strains temperature-sensitive to the biotin action-suppressing agent may be available other than the method based on the mutation treatment described above. For example, a gene relevant to resistance to the biotin action-suppressing agent is obtained from a coryneform L-glutamic acid-producing bacterium, and the gene is subjected to a mutation treatment in vitro to obtain a mutant type gene which gives the resistance to the biotin action-suppressing agent in a temperature sensitive way. Next, a corresponding wild type gene on chromosome is substituted with the mutant type gene by using an already established technique for homologous recombination. Thus a mutant strain temperature-sensitive to the biotin action-suppressing agent can be obtained.

A gene relevant to surfactant resistance will be described below as a gene relevant to the resistance to the biotin action-suppressing agent. A gene relevant to surfactant resistance originating from a coryneform bacterium may be isolated by:

(1) obtaining a surfactant-sensitive mutant strain belonging to the coryneform bacteria having increased sensitivity to a surfactant;
(2) ligating various chromosomal DNA fragments of a wild type coryneform bacterium with a vector capable of operation in the coryneform bacteria to prepare various recombinant DNA's;
(3) introducing the various recombinant DNA's into the surfactant-sensitive mutant strain belonging to the coryneform bacteria to perform transformation;
(4) selecting a strain with lost surfactant sensitivity, that is, a strain with increased surfactant resistance from transformed strains;
(5) recovering recombinant DNA from the transformed strain with lost surfactant sensitivity; and
(6) analyzing the structure of a chromosomal DNA fragment of the wild type coryneform bacterium ligated with the vector.

The chromosomal DNA fragment of the wild type coryneform bacterium thus obtained contains the gene relevant to the surfactant resistance originating from the coryneform bacterium. This gene at least relates to a mechanism of the coryneform bacterium to produce L-glutamic acid in a medium containing a surfactant. At the same time, it also has a possibility of common relation to production of L-glutamic acid by means of addition of penicillin or restriction of biotin.

In the item (1) described above, the "surfactant-sensitive mutant strain belonging to the coryneform bacteria having increased sensitivity to surfactant" refers to a mutant strain belonging to the coryneform bacteria with deteriorated growth in a medium in which a surfactant exists at a concentration at which no influence is exerted on growth of the wild type coryneform bacterium. For example, when polyoxyethylene sorbitan monopalmitate is used as the surfactant, the surfactant-sensitive mutant strain belonging to the coryneform bacteria makes poor growth as compared with the wild strain if the surfactant is added to a medium at a concentration of 0.1–1 mg/dl. On the other hand, the wild type coryneform bacterium makes no observable change in growth even in a medium in which the surfactant is added at a concentration of 0.1–1 mg/dl. The concentration of the surfactant required for L-glutamic acid production decreases, as compared with an ordinary case, when such a surfactant-sensitive mutant strain is cultivated to produce L-glutamic acid by adding the surfactant. It is postulated that cells of the surfactant-sensitive mutant strain have a state which is approximate to a state of cells of the wild strain exposed to the surfactant.

Preparation of Gene Relevant to Surfactant Sensitivity

In order to obtain the surfactant-sensitive mutant strain belonging to the coryneform bacteria, a method described in Japanese Patent Publication No. 52-24593 can be used. Namely, a mutation-inducing treatment such as ultraviolet light irradiation, X-ray irradiation, radiation irradiation, and mutating agent treatments is applied to a coryneform glutamic acid-producing bacterium to obtain a strain which cannot grow on an agar medium containing a surfactant in an amount with which the parent strain grows.

The surfactant-sensitive mutant strain belonging to the coryneform bacteria is specifically exemplified by *Brevibacterium lactofermentum* AJ11060, which is disclosed in Japanese Patent Publication No.59-10797.

The method for preparing various chromosomal DNA fragments of the wild type coryneform bacterium is as follows. Namely, the wild type coryneform bacterium is cultivated in a liquid medium, and chromosomal DNA is recovered from collected cells in accordance with a method of Saito et al. (H. Saito and K. Miura, *Biochem. Biophys. Acta*, 72, 619 (1963)). Recovered chromosomal DNA is digested with a restriction enzyme. A variety of DNA fragments can be prepared by conducting a reaction under a condition to incompletely decompose DNA by using an enzyme of a four-nucleotide recognition type as the restriction enzyme.

The vector capable of operation in the coryneform bacteria is, for example, a plasmid capable of autonomous replication in the coryneform bacteria. Specifically, it can be exemplified by the followings.
(1) pAM330 (see Japanese Patent Laid-open No. 58-67699)
(2) pHM1519 (see Japanese Patent Laid-open No. 58-77895)
(3) pAJ655 (see Japanese Patent Laid-open No. 58-192900)
(4) pAJ611 (see the same)
(5) pAJ1844 (see the same)
(6) pCG1 (see Japanese Patent Laid-open No. 57-134500)
(7) pCG2 (see Japanese Patent Laid-open No. 58-35197)
(8) pCG4 (see Japanese Patent Laid-open No. 57-183799)
(9) pCG11 (see the same)

In order to ligate the vector capable of operation in the coryneform bacteria with various chromosomal DNA fragments of the wild type coryneform bacterium to prepare various recombinant DNA's, the vector is digested with the same restriction enzyme as the restriction enzyme used to digest chromosomal DNA, or with a restriction enzyme which generates a terminal sequence complementary to a terminal sequence of various chromosomal DNA fragments. The digested vector is usually ligated with the chromosomal DNA fragments by using a ligase such as T4 DNA ligase.

In order to introduce the various recombinant DNA's into the surfactant-sensitive mutant strain belonging to the coryneform bacteria, a procedure may be carried out in accordance with conventional and reported transformation methods. For example, it is possible to use a method in which recipient cells are treated with calcium chloride to increase permeability of DNA as reported for *Escherichia coli* K-12 (Mandel, M. and Higa, A., *J. Mol. Biol.*, 53, 159 (1970)), and a method in which competent cells are prepared from cells at a proliferating stage to introduce DNA as reported for *Bacillus subtilis* (Duncan, C. H., Wilson, G. A. and Yound, F. E., *Gene*, 1, 153 (1977)). Alternatively, it is also possible to apply a method in which DNA recipient cells are converted into a state of protoplasts or spheroplasts which easily incorporate recombinant DNA to introduce recombinant DNA into DNA recipients as known for *Bacillus subtilis*, actinomycetes, and yeast (Chang, S and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978)).

As for the protoplast method, a sufficiently high frequency can be obtained even by using the method used for *Bacillus subtilis* described above. However, as disclosed in Japanese Patent Laid-open No. 57-183799, it is also possible to utilize a method in which DNA is allowed to be incorporated in a state in which protoplasts of coryneform bacterial cells contact with divalent metal ion and one of polyethylene glycol or polyvinyl alcohol. Incorporation of DNA can be also facilitated by addition of carboxymethyl cellulose, dextran, Ficoll, Pluronic F68 (Serva) and the like, in place of polyethylene glycol or polyvinyl alcohol. An electric pulse method (see Japanese Patent Laid-open No. 2-207791) was used in Example of the present invention as a method for transformation.

A method for selecting strains with lost surfactant sensitivity from transformed strains will be described below.

DNA fragments having sizes of about 4–6 Kbp obtained by partially digesting chromosomal DNA of a wild strain of a coryneform bacterium with a restriction enzyme Sau3AI are ligated with a plasmid vector capable of autonomous proliferation in both *Escherichia coli* and coryneform bacteria to produce recombinant DNA's which are introduced into competent cells of *Escherichia coli* DH5 strain (produced by Takara Shuzo Co., Ltd.) or the like. Transformed strains are cultivated to construct a gene library of the wild strain of the coryneform bacterium.

The surfactant-sensitive mutant strain AJ11060 is transformed with recombinant DNA's contained in the gene library described above. Obtained transformants are once spread on M-CM2G agar plates (containing glucose 5 g, polypeptone 10 g, yeast extract 10 g, NaCl 5 g, DL-methionine 0.2 g, agar 15 g, and chloramphenicol 4 mg in 1 l of pure water, pH 7.2) containing no surfactant to form about 40,000 colonies. The colonies are replicated on M-CM2G plates containing 30 mg/L of a surfactant (Tween 40) to obtain those exhibiting good growth on the M-CM2G plates containing the surfactant. Thus strains with lost surfactant sensitivity can be obtained.

The same method as the method for preparing chromosomal DNA of wild type coryneform bacteria may be used to recover recombinant DNA from a transformed strain with lost surfactant sensitivity. Namely, the transformed strain is cultivated in a liquid medium, and recombinant DNA can be recovered from collected cells in accordance with a method of Saito et al. (H. Saito and K. Miura, *Biochem. Biophys. Acta*, 72, 619 (1963)).

The structure of the chromosomal DNA fragment of the wild type coryneform bacterium ligated with the vector is analyzed, for example, as follows. An entire nucleotide sequence of the chromosomal DNA fragment is determined by a dideoxy method which is an ordinary method for nucleotide sequencing. The structure of DNA is analyzed to determine existing positions of enhancer, promoter, operator, SD sequence, leader peptide, attenuator, initiation codon, termination codon, open reading frame and so on.

One of genes relevant to surfactant resistance originating from a coryneform bacterium obtained as described above in Example 3 described below was designated as "dtsR gene". This dtsR gene at least has a sequence from 467-469th ATG to 1985-1987th CTG of a nucleotide sequence shown in SEQ ID NO: 1 in Sequence Listing. An amino acid sequence which can be encoded by this gene is shown in SEQ ID NOS: 1 and 2 in Sequence Listing. Another ATG (nucleotide Nos. 359–361) exists in the same frame at a position upstream from the aforementioned 467-469th ATG. It is impossible to deny the possibility that the additional ATG is the initiation codon. However, it is postulated that the aforementioned 467-469th ATG is the initiation codon according to analysis of a consensus sequence existing in a region upstream from this gene. Namely, it is postulated that the dtsR gene codes for a peptide having an amino acid sequence comprising amino acid Nos. 37–543 in the amino acid sequence shown in SEQ ID NO: 2. This peptide was designated as "DTSR protein". When the amino acid sequence of the DTSR protein and the nucleotide sequence of the dtsR gene are referred to in the specification and claims of the present invention, they may be generally described by using 467-469th ATG as the initiation codon. However, the possibility of 359-361th ATG as the initiation codon should be also taken into consideration. For example, when it is intended to introduce the dtsR gene into a bacterium belonging to the genus Corynebacterium to enhance its expression, it is assumed that a sequence comprising nucleotide Nos. 467–1987 in the nucleotide sequence shown in SEQ ID NO: 1 may be expressed. However, it will be easily understood by those skilled in the art that the DTSR protein can be correctly expressed regardless of any ATG as the initiation codon, if a coding region and an upstream region of the nucleotide sequence shown in SEQ ID NO: 1 including nucleotide Nos. 359–466 are introduced into the bacterium belonging to the genus Corynebacterium. When the dtsR gene is expressed in bacterial cells, Met at the N-terminal encoded by the initiation codon is occasionally cut by aminopeptidase.

As shown in Example 3 described below, it has been revealed that the amino acid sequence of the DTSR protein has homology to a protein having been already reported. The protein is described as β-subunit of propionyl-CoA carboxylase (PPC) protein in *Proc. Natl. Acad. Sci. USA*, vol. 83 (1986) 8049–8053; *Proc. Natl. Acad. Sci. USA*, vol. 83 (1986) 4864–4868; and *Gene*, vol. 122 (1992) 199–202. Any of these literatures has no description which suggests that the protein relates to glutamic acid productivity.

Propionyl-CoA carboxylase is an enzyme which catalyzes a reaction in a metabolic pathway to convert α-ketoglutarate into succinyl-CoA through 2-hydroxyglutarate, propionyl-CoA, D-methylmalonyl-CoA, and L-methylmalonyl-CoA. This metabolic pathway is probably a pathway to bypass a reaction catalyzed by α-ketoglutarate dehydrogenase in the TCA cycle. In addition, propionyl-CoA carboxylase is an enzyme which uses biotin as a coenzyme. According to these facts, it is suggested that the reaction catalyzed by propionyl-CoA carboxylase, and the aforementioned metabolic pathway or a part thereof including the reaction relate to the surfactant resistance. Therefore, it is highly probable that the genes relevant to the surfactant resistance include genes coding for α-subunit of propionyl-CoA carboxylase, or other enzymes or subunit thereof for catalyzing each of the reactions of the aforementioned metabolic pathway, in addition to the dtsR gene. Further, the present inventors have found that a DTSR protein-deficient strain requires oleic acid for cultivation. Acetyl-CoA carboxylase which uses biotin as a coenzyme has a similar structure to that of propionyl-CoA carboxylase. Thus genes coding for enzymes or subunits thereof for catalyzing each of reactions of the fatty acid metabolism pathway probably relate to the surfactant resistance, as well. The "mutation to exhibit temperature sensitivity to the biotin action-suppressing agent" of the present invention may also include mutation on such genes.

Preparation of Mutant Type dtsR Gene-Introduced Strain by Gene Substitution

The temperature-sensitive mutation to surfactants can be also given by generating mutation on the gene relevant to the surfactant resistance as represented by the dtsR gene obtained as described above. Namely, a procedure may be carried out by introducing mutation in vitro into the obtained gene to prepare a mutant type gene which provides a temperature-sensitive function of its gene product, and substituting the wild type gene existing on chromosome with the mutant type gene by means of homologous gene recombination. Gene substitution by homologous recombination has been already established. It is possible to utilize, for example, a method using linear DNA, or a method using temperature-sensitive plasmid.

Specifically, the modification of the dtsR gene into a mutant type gene is performed by causing substitution, deletion, insertion, addition, or inversion of one or more nucleotides in a nucleotide sequence of a coding region or a promoter region of the dtsR gene by means of a site-directed mutagenesis method (Kramer, W. and Frits, H. J., *Methods in Enzymology*, 154, 350 (1987)), or a treatment with a chemical reagent such as sodium hypochlorite and hydroxylamine (Shortle, D. and Nathans, D., *Proc. Natl. Acad. Sci. U.S.A.*, 75, 270 (1978)).

The site-directed mutagenesis method is a method of using synthetic oligonucleotides, which is a technique to enable introduction of optional substitution, deletion, insertion, addition, or inversion only into optional and limited base pairs. When this method is utilized, at first a plasmid having a cloned dtsR gene with determined nucleotide sequence is denatured to prepare single-strand DNA. Next, a synthetic oligonucleotide complementary to a portion intended to cause mutation is used. However, the synthetic oligonucleotide is not allowed to have a completely complementary sequence, but allowed to have optional base substitution, deletion, insertion, addition, or inversion. The single-strand DNA is annealed with the synthetic oligonucleotide having optional base substitution, deletion, insertion, addition, or inversion. A complete double-strand plasmid is synthesized by using T4 ligase and Klenow fragment of DNA polymerase I, and it is introduced into competent cells of *Escherichia coli*. Some transformants thus obtained have plasmids containing genes in which optional base substitution, deletion, insertion, addition, or inversion is fixed. Similar techniques to introduce gene mutation include a recombinant PCR method (*PCR Technology*, Stockton press (1989)).

The method using a chemical reagent treatment is a method in which mutation having base substitution, deletion, insertion, addition, or inversion is randomly introduced into a DNA fragment by treating the DNA fragment containing an objective gene directly with sodium hypochlorite, hydroxylamine or the like.

The method for substituting a normal gene on chromosome of a coryneform L-glutamic acid-producing bacterium with the mutation-introduced gene thus obtained includes a method which utilizes homologous recombination (*Experiments in Molecular Genetics*, Cold Spring Harbor Laboratory press (1972); Matsuyama, S. and Mizushima, S., *J. Bacteriol.*, 162, 1196 (1985)). In the homologous recombination, when a plasmid or the like which has a sequence having homology to a sequence on chromosome is introduced into a bacterial cell, recombination takes place at a certain frequency at a position of the sequence having homology, and the entire introduced plasmid is incorporated into the chromosome. When further recombination takes place thereafter at a position of the sequence having homology on the chromosome, the plasmid falls off from the chromosome. At this time, the mutation-introduced gene is sometimes preferentially fixed on the chromosome depending on the position at which recombination takes place, and the original normal gene falls off from the chromosome together with the plasmid. By selecting such a bacterial strain, it is possible to obtain a bacterial strain in which the normal gene on the chromosome is substituted with the mutation-introduced gene having base substitution, deletion, insertion, addition, or inversion.

[3] Improvement in L-Glutamic Acid Productivity of Surfactant Temperature-Sensitive Mutant Strain by Enhancement of Genes of Glutamic Acid Biosynthesis System The L-glutamic acid productivity of the surfactant temperature-sensitive mutant strain of the L-glutamic acid-producing bacterium can be improved by enhancing genes of the glutamic acid biosynthesis system. The genes of the glutamic acid biosynthesis system having been enhanced in cells include, for example, phosphofructokinase of the glycolytic pathway (PFK, Japanese Patent Laid-open No. 63-102692), phosphoenolpyruvate carboxylase of an anaplerotic pathway (PEPC, Japanese Patent Laid-open Nos. 60-87788 and 62-55089), citrate synthase of the TCA cycle (CS, Japanese Patent Laid-open Nos. 62-201585 and 63-119688), aconitate hydratase (ACO, Japanese Patent Laid-open No. 62-294086), isocitrate dehydrogenase (ICDH, Japanese Patent Laid-open Nos. 62-166890 and 63-214189), and glutamate dehydrogenase which catalyzes amination reaction (GDH, Japanese Patent Laid-open No. 61-268185).

Several methods as described below may be available in order to obtain the aforementioned genes.

(1) A mutant strain is obtained in which a characteristic character is exhibited as a result of occurrence of mutation on an objective gene, and the character disappears by introducing the objective gene. A gene which complements the character of the mutant strain is obtained from chromosome of a coryneform bacterium.

(2) If an objective gene has been already obtained from another organism, and its nucleotide sequence has been clarified, then the objective gene is obtained by means of a technique of hybridization using DNA in a region having high homology as a probe.

(3) If a nucleotide sequence of an objective gene has been revealed fairly in detail, then a gene fragment containing the objective gene is obtained by means of a PCR method (Polymerase Chain Reaction Method) using chromosome of a coryneform bacterium as a template.

The chromosome used herein can be obtained in accordance with the method of Saito et al. described above (H. Saito and K. Miura, *Biochem. Biophys. Acta* 72, 619 (1963)). Any host-vector system available in the coryneform bacteria may be used, and those having been described above may be used. The method in the aforementioned item (3), which is effective when the nucleotide sequence has been clarified, was used in Example of the present invention described below.

When a gene is obtained in accordance with the methods of the items (2) and (3) described above, an objective gene occasionally has no unique promoter. In such a case, the objective gene can be expressed by inserting a DNA fragment having promoter activity in the coryneform bacteria into a position upstream from the objective gene. In order to enhance expression of an objective gene, it may be available that the objective gene is ligated at a position downstream from a strong promoter. Strong promoters among promoters which operate in cells of the coryneform bacteria include, for example, lac promoter, tac promoter, and trp promoter of *Escherichia coli* (Y. Morinaga, M. Tsuchiya, K. Miwa and K. Sano, *J. Biotech.*, 5, 305–312 (1987)). In addition, trp promoter of the coryneform bacteria is also a preferable promoter (Japanese Patent Laid-open No. 62-195294). The trn promoter of the coryneform bacteria was used for expression of PEPC gene in Example of the present invention described below.

[4] Production of L-Glutamic Acid by Surfactant Temperature-Sensitive Mutant Strain Originating from L-Glutamic Acid-Producing Bacterium The method of producing L-glutamic acid according to the present invention comprises cultivating, in a liquid medium, the surfactant temperature-sensitive mutant strain originating from the L-glutamic acid-producing bacterium obtained as described above, producing and accumulating L-glutamic acid in the medium, and collecting it from the medium.

An ordinary nutrient medium containing a carbon source, a nitrogen source, inorganic salts, growth factors, etc. is used as the liquid medium for the cultivation of the aforementioned mutant strain according to the present invention. The mutant strain of the present invention has an ability to produce L-glutamic acid without allowing any biotin action-suppressing agent to be contained in a medium even in the case of cultivation in any liquid medium containing an excessive amount of biotin.

Carbohydrates such as glucose, fructose, sucrose, waste molasses, starch hydrolysate; alcohols such as ethanol and glycerol; and organic acids such as acetic acid may be used as the carbon source. Ammonium sulfate, ammonium nitrate, ammonium chloride, ammonium phosphate, ammonium acetate, ammonia, peptone, meat extract, yeast extract, corn steep liquor, etc. may be used as the nitrogen source. When a mutant strain having an auxotrophy is used, a required substance is added as a preparation or a natural material containing it.

Fermentation is performed for 2–7 days under an aerobic condition achieved by shaking cultivation, aerating and agitating cultivation or the like while maintaining pH of culture liquid at 5–9. pH is adjusted by using urea, calcium carbonate, ammonia gas, aqueous ammonia and the like. The cultivation temperature is 24°–37° C. However, a better result is obtained by initiating cultivation at about 31.5° C., and raising the temperature to 33°–40° C., preferably about 37° C. at an intermediate stage of the cultivation. Namely, the bacterium is sufficiently proliferated in the vicinity of a temperature optimum for growth, and then the temperature is raised during cultivation. Thus production of L-glutamic acid is initiated without adding any biotin action-suppressing agent, and L-glutamic acid is produced and accumulated in a considerable amount in a culture liquid.

The present inventors have found that a DTSR protein-deficient strain has an ability to produce L-glutamic acid without allowing any biotin action-suppressing agent to be contained in a medium even in the case of cultivation in any liquid medium containing an excessive amount of biotin. The DTSR protein-deficient strain requires oleic acid for its cultivation. However, the surfactant temperature-sensitive strain does not require addition of oleic acid when it is cultivated at an ordinary temperature, namely about 31.5° C.

Collection of L-glutamic acid produced and accumulated in the culture liquid may be carried out in accordance with an ordinary method. For example, a method of ion exchange resin, a method of crystallization, etc. may be used. Specifically, L-glutamic acid is adsorbed and separated by using an anion exchange resin, or crystallized by neutralization.

<2> PREPARATION OF SURFACTANT TEMPERATURE-SENSITIVE MUTANT STRAIN HAVING L-LYSINE PRODUCTIVITY, AND PRODUCTION OF L-LYSINE AND L-GLUTAMIC ACID

When a conventional and known L-lysine-producing bacterium originating from a coryneform L-glutamic acid-producing bacterium is cultivated in a medium containing an excessive amount of biotin of not less than 10 $\mu$g/L, it produces and accumulates only L-lysine in a culture liquid and produces substantially no L-glutamic acid as well in the same manner as the L-glutamic acid-producing bacterium described above, unless a biotin action-suppressing agent such as surfactants or antibiotics is allowed to be contained in the medium at an initial or intermediate stage of cultivation. The mutant strain to be used in the present invention has an ability to produce both L-lysine and L-glutamic acid without allowing any biotin action-suppressing agent to be contained in a medium even when it is cultivated in any liquid medium containing an excessive amount of biotin. Such a mutant strain has the L-lysine productivity in addition to the property of the surfactant temperature-sensitive mutant strain of the L-glutamic acid-producing bacterium described above. Namely, the second mutant strain of the present invention is a mutant strain originating from a coryneform L-glutamic acid-producing bacterium, having mutation to give L-lysine productivity and temperature-sensitive mutation to a biotin action-suppressing agent, and having an ability to produce both L-lysine and L-glutamic acid in the absence of any biotin action-suppressing agent in a medium containing an excessive amount of biotin.

The L-lysine productivity can be usually given by using resistant mutation to S-(2-aminoethyl)-L-cysteine (hereinafter sometimes abbreviated as "AEC") (Japanese Patent Publication No. 48-28078). Other L-lysine-producing mutant strains include, for example, a mutant strain which requires amino acid such as L-homoserine for its growth (Japanese Patent Publication No. 56-6499); a mutant strain which exhibits resistance to AEC and requires amino acids such as L-leucine, L-homoserine, L-proline, L-serine, L-arginine, L-alanine, and L-valine (U.S. Pat. Nos. 3,708, 395 and 3,825,472); an L-lysine-producing mutant strain which exhibits resistance to DL-α-amino-ε-caprolactam, α-amino-lauryllactam, aspartate-analog, sulfa drug, quinoid, N-lauroylleucine; an L-lysine-producing mutant strain which exhibits resistance to inhibitors of oxyaloacetate decarboxylase or respiratory system enzymes (Japanese Patent Laid-open Nos. 50-53588, 50-31093, 52-102498, 53-9394, 53-86089, 55-9783, 55-9759, 56-32995 and 56-39778, and Japanese Patent Publication Nos. 53-43591 and 53-1833); an L-lysine-producing mutant strain which requires inositol or acetic acid (Japanese Patent Laid-open Nos. 55-9784 and 56-8692); an L-lysine-producing mutant strain which exhibits sensitivity to fluoropyruvic acid or temperature not less than 34° C. (Japanese Patent Laid-open Nos. 55-9783 and 53-86090); and an L-lysine producing mutant strain (U.S. Pat. No. 4,411,997).

The second mutant strain of the present invention can be induced, for example, by giving temperature sensitivity to a biotin action-suppressing agent such as surfactants and antibiotics to an L-lysine-producing bacterium originating from a coryneform L-glutamic acid-producing bacterium.

The temperature sensitivity can be given in the same manner as the introduction of temperature sensitivity into the first mutant strain of the present invention as described in the item <1> described above. Namely, the bacterial strain having temperature sensitivity to the biotin action-suppressing agent can be obtained by applying a mutation treatment such as ultraviolet light irradiation, X-ray irradiation, radiation irradiation, and mutating agent treatments to a coryneform glutamic acid-producing bacterium having L-lysine productivity, followed by conducting a replica method on an agar plate medium containing the biotin action-suppressing agent. Namely, the growth state of a parent strain in the presence of several concentrations of the biotin action-suppressing agent is observed at a cultivation temperature of 33°–37° C., preferably not less than 34° C. to determine a maximum concentration of the biotin action-suppressing agent at which growth is recognized. A mutant strain may be separated which cannot grow or has a remarkably lowered growth speed in the presence of the biotin action-suppressing agent at the maximum concentration at the same temperature as that used above. Alternatively, as shown in the item <1> [2], a mutant strain temperature-sensitive to the biotin action-suppressing agent may be obtained by genetic recombination.

Alternatively, the second mutant strain to be used in the present invention can be also obtained by previously inducing a mutant strain temperature-sensitive to the biotin action-suppressing agent from a coryneform L-glutamic acid-producing bacterium, followed by giving L-lysine productivity to the mutant bacterial strain.

The temperature sensitivity to the biotin action-suppressing agent and the L-lysine productivity are given to the coryneform L-glutamic acid-producing bacterium as described above. Thus the mutant strain can be bred which has the ability to produce both L-lysine and L-glutamic acid in the absence of any biotin action-suppressing agent in a medium containing an excessive amount of biotin.

As described in the item <1> [3], the productivity of L-glutamic acid can be improved for the second mutant strain of the present invention by enhancing genes of the glutamic acid biosynthesis system as described above. In the same manner, the L-lysine productivity can be improved by enhancing genes of the lysine biosynthesis system.

Known examples of the genes of the lysine biosynthesis system having been enhanced in cells include a gene coding for aspartokinase α-subunit protein or β-subunit protein in which concerted feedback inhibition by L-lysine and L-threonine is substantially desensitized (WO94/25605 International Publication Pamphlet), a wild type phosphoenolpyruvate carboxylase gene originating from a coryneform bacterium (Japanese Patent Laid-open No. 60-87788), a gene coding for wild type dihydrodipicolinate synthetase originating from a coryneform bacterium (Japanese Patent Publication No. 6-55149), etc.

An ordinary nutrient medium containing a carbon source, a nitrogen source, inorganic salts, growth factors, etc., which is similar to that used for cultivation of the first mutant strain described above, is used as a liquid medium for cultivation of the second mutant strain of the present invention. The second mutant strain of the present invention has an ability to produce L-lysine and L-glutamic acid without allowing any biotin action-suppressing agent to be contained in a medium even in the case of cultivation in any liquid medium containing an excessive amount of biotin.

Fermentation is performed for 2–7 days under an aerobic condition achieved by shaking cultivation, agitating and aerating cultivation or the like while maintaining pH of culture liquid at 5–9. pH is adjusted by using urea, calcium carbonate, ammonia gas, aqueous ammonia and the like. The cultivation temperature is 24°–37° C. However, a better result is obtained by initiating cultivation at about 31.5° C., and raising the temperature to 33°–40° C., preferably about 37° C. at an intermediate stage of the cultivation. Namely, L-lysine is mainly produced at about 31.5° C., but the rate of L-glutamic acid production is increased by raising the temperature during the cultivation. By utilizing this phenomenon, it is possible to control the ratio of L-lysine to L-glutamic acid in a culture liquid to be finally obtained as desired.

An ordinary method may be used for collecting L-lysine and L-glutamic acid produced and accumulated in the culture liquid. For example, a method of ion exchange resin, a method of crystallization, etc. may be used. When the method of ion exchange resin is used, L-lysine is firstly adsorbed and separated from the culture liquid by using a cation exchange resin, and then L-glutamic acid is adsorbed and separated by using an anion exchange resin, or crystallized by neutralization. When L-lysine and L-glutamic acid are used as a mixture, it is of course unnecessary to separate these amino acids with each other.

BEST MODE FOR CARRYING OUT THE INVENTION

Figure 1:
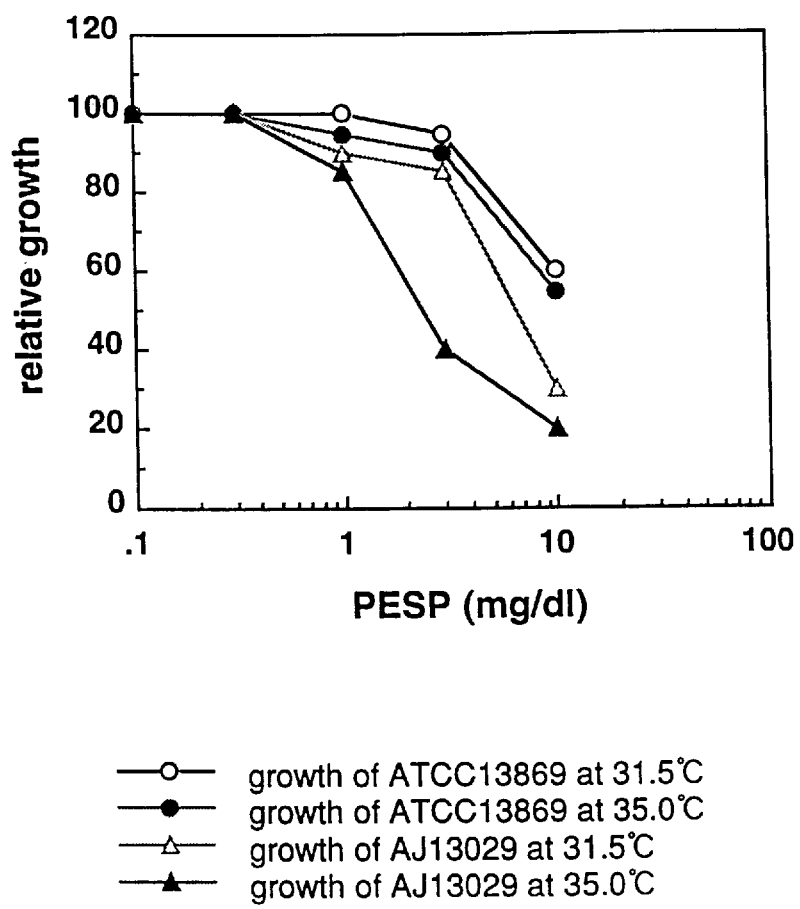
FIG. 1 shows influences exerted by PESP on growth of Brevibacterium lactofermentum AJ13029 and its parent strain ATCC 13869 at 31.5° C. and 35° C.

The present invention will be more specifically explained below with reference to Examples.

EXAMPLE 1

Preparation of Mutant Strain Temperature-Sensitive to Biotin Action-Suppressing Agent Originating from Coryneform L-Glutamic Acid-Producing Bacterium 1. Measurement of Sensitivity of L-Glutamic Acid-Producing Bacterium to Biotin Action-Suppressing Agent by Replica Method Sensitivity of *Brevibacterium lactofermentum* ATCC 13869 to polyoxyethylene sorbitan monopalmitate (PESP) was measured as follows in accordance with a replica method.

*Brevibacterium lactofermentum* ATCC 13869 was cultivated overnight at 31.5° C. on a CM2B agar plate medium having a composition shown in Table 1 to obtain bacterial cells. They were suspended in sterilized physiological saline, seeded on the aforementioned agar plate medium, and cultivated at 31.5° C. for 20–30 hours to form colonies. They were replicated on a CM2B agar medium added with each concentration of PESP, and cultivated at 35° C. for 20–30 hours to observe the growth state.

TABLE 1

| Component | Concentration |
|---|---|
| Polypeptone (produced by Nihon Pharmaceutical) | 1.0% |
| Yeast extract (produced by Difco) | 1.0% |
| NaCl | 0.5% |
| D-biotin | 10 μg/l |
| Agar | 1.5% | pH 7.2

As a result, it was confirmed that the growth-permitting concentration had a threshold value in the vicinity of 3 mg/dl of PESP concentration at 35° C. as shown in Table 2.

TABLE 2

| PESP concentration (mg/dl) | 0 | 0.1 | 0.3 | 1.0 | 3.0 | 10 | 30 |
|---|---|---|---|---|---|---|---|
| Colony formation | + | + | + | + | + | − | − |

2. Induction of Mutant Strain Exhibiting Temperature Sensitivity to Biotin Action-Suppressing Agent

*Brevibacterium lactofermentum* ATCC 13869 was cultivated on a bouillon agar medium at 31.5° C. for 24 hours to obtain bacterial cells. The obtained bacterial cells were treated at 30° C. for 30 minutes with an aqueous solution of 250 μg/ml of N-methyl-N'-nitro-N-nitrosoguanidine. A suspension of the bacterial cells at a survival ratio of 1% was then seeded on a CM2B agar plate medium, and cultivated at 31.5° C. for 20–30 hours to form colonies. They were replicated on a CM2B agar medium and a CM2B agar medium added with 3 mg/dl of PESP respectively, and cultivated at 35° C. for 20–30 hours. Bacterial strains were obtained, which grew on the CM2B medium but made no observable growth on the CM2B medium containing 3 mg/dl of PESP. Thus 720 strains were obtained from about 10,000 colonies. Each of the obtained bacterial strains was reconfirmed for the presence or absence of growth at 35° C. on the CM2B agar plate medium containing 3 mg/dl of PESP. Strains which apparently exhibited no sensitivity were excluded, and 435 strains which exhibited sensitivity were obtained.

3. Confirmation of L-Glutamic Acid Productivity of Mutant Strains Exhibiting Temperature Sensitivity to Biotin Action-Suppressing Agent The L-glutamic acid productivity was confirmed as follows for the 435 mutant strains obtained in the item 2. described above and their parent strain ATCC 13869.

ATCC 13869 strain and each of the mutant strains were cultivated on the CM2B agar medium at 31.5° C. for 20–30 hours respectively to obtain bacterial cells which were seeded in a liquid medium having a composition of Medium A in Table 3 to start cultivation with shaking at 31.5° C. After about 22 hours, a medium was newly added so that final concentrations were shown in Medium B in Table 3, followed by performing cultivation for about 24 hours at 31.5° C. or after shifting the cultivation temperature to 35° C. or 37° C. After completion of the cultivation, the presence or absence of L-glutamic acid production was investigated by using a Biotech Analyzer produced by Asahi Chemical Industry. As a result, it was confirmed that 106 strains among the 435 mutant strains produced glutamic acid.

TABLE 3

| Component | Medium A | Medium B |
|---|---|---|
| Glucose | 3 g/dl | 5 g/dl |
| $KH_2PO_4$ | 0.14 g/dl | 0.14 g/dl |
| $MgSo_4 \cdot 7H_2O$ | 0.04 g/dl | 0.04 g/dl |
| $FeSO_4 \cdot 7H_2O$ | 0.001 g/dl | 0.001 g/dl |
| $MnSO_4 \cdot 4H_2O$ | 0.001 g/dl | 0.001 g/dl |
| $(NH_4)_2SO_4$ | 1.5 g/dl | 2.5 g/dl |
| Soybean protein hydrolysate solution | 1.5 ml/dl | 0.38 ml/dl |
| Thiamin hydrochloride | 0.2 mg/l | 0.2 mg/l |
| Biotin | 0.3 mg/l | 0.3 mg/l |
| Antifoaming agent | 0.05 ml/l | 0.05 ml/l |
| $CaCO_3$ | 5 g/dl | 5 g/dl | pH 7.0 (adjusted with KOH)

Accumulation amounts of L-glutamic acid at each temperature are shown in Table 4 for representative strains of the mutant strains and ATCC 13869 strain.

TABLE 4

Accumulation of glutamic acid by mutant strains (g/dl)

| | Cultivation temperature after temperature shift | | |
|---|---|---|---|
| Bacterial strain | 31.5° C. | 35° C. | 37° C. |
| ATCC 13869 | 0.0 | 0.0 | 0.2 |
| No. 21 | 0.3 | 2.8 | 2.9 |
| No. 36 | 2.4 | 2.6 | 2.7 |
| No. 58 | 0.2 | 1.9 | 2.7 |
| No. 100 | 0.4 | 1.5 | 2.8 |
| No. 121 | 0.5 | 1.7 | 1.9 |

4. Confirmation of Temperature Sensitivity to Biotin Action-Suppressing Agent

Temperature sensitivity to PESP of the mutant strains obtained in the item 3. described above was confirmed as follows by means of liquid culture.

Each of the mutant strains and their parent strain were cultivated on the CM2B agar plate medium at 31.5° C. for 24 hours to obtain bacterial cells. The obtained bacterial cells were inoculated to a CM2B liquid medium and a CM2B liquid medium containing PESP at a concentration of 3 mg/dl to perform cultivation with shaking at 31.5° C. and 37° C. for 24 hours. Optical densities of obtained culture liquids were measured at 660 nm. The relative growth degree in the PESP-added medium was determined provided that growth in the medium without addition of PESP at each temperature was regarded as 100. Results are shown in Table 5.

TABLE 5

| Bacterial strain | Relative Growth degree | |
|---|---|---|
| | 31.5° C. | 37° C. |
| ATCC 13869 | 98 | 85 |
| No. 21 | 81 | 33 |
| No. 36 | 52 | 15 |
| No. 58 | 85 | 32 |
| No. 100 | 82 | 32 |
| No. 121 | 95 | 40 |

As shown in this table, *Brevibacterium lactofermentum* ATCC 13869 as a parent strain had a relative growth degree of 85 at 37° C. in the presence of 3 mg/dl of PESP, while each of the mutant strains had a relative growth degree of 40 or less in the presence of PESP, clearly having sensitivity to PESP at a concentration of 3 mg/dl.

The relative growth degree at 31.5° C. and 35° C. in the presence of several concentrations of PESP is shown in FIG. 1 for the mutant strain No. 21 among the mutant strains obtained in the item 3. described above and its parent strain ATCC 13869.

Among the mutant strains, No. 21 has been designated as *Brevibacterium lactofermentum* AJ13029, deposited on Sep. 2, 1994 in National Institute of Bioscience and Human Technology of Agency of Industrial Science and Technology under a deposition number of FERM P-14501, transferred to international deposition based on the Budapest Treaty on Aug. 1, 1995, and awarded a deposition number of FERM BP-5189.

EXAMPLE 2

Production of L-Glutamic Acid

1. Investigation on Cultivation Temperature Shift Timing

*Brevibacterium lactofermentum* ATCC 13869 or AJ13029 was inoculated to a seed culture medium having a composition shown in Table 6, and cultivated with shaking at 31.5° C. for 24 hours to obtain a seed culture. A medium for full-scale cultivation having a composition shown in Table 6 was dispensed into each amount of 300 ml and poured into a jar fermenter made of glass having a volume of 500 ml, and sterilized by heating. After that, 40 ml of the seed culture was inoculated thereto. Cultivation was started by using an agitation speed of 800–1,300 rpm, an aeration amount of 1/2–1/1 vvm, and a cultivation temperature of 31.5° C. The culture liquid was maintained to have pH of 7.5 by using ammonia gas. The cultivation temperature was shifted to 37° C., 8, 12 or 16 hours after the start of cultivation. A control for comparison was provided in which the cultivation temperature was not shifted, and cultivation was continued exactly at 31.5° C.

TABLE 6

| Component | Concentration | |
|---|---|---|
| | Seed culture | Full-scale culture |
| Glucose | 5 g/dl | 15 g/dl |
| $KH_2PO_4$ | 0.1 g/dl | 0.2 g/dl |
| $MgSO_4 \cdot 7H_2O$ | 0.04 g/dl | 0.15 g/dl |
| $FeSO_4 \cdot 7H_2O$ | 1 mg/dl | 1.5 mg/dl |
| $MnSO_4 \cdot 4H_2O$ | 1 mg/dl | 1.5 mg/dl |
| Soybean protein hydrolysate solution | 2 ml/dl | 5 ml/dl |

TABLE 6-continued

| Component | Concentration | |
|---|---|---|
| | Seed culture | Full-scale culture |
| Biotin | 50 μg/l | 200 μg/l |
| Thiamin hydrochloride | 200 μg/l | 300 μg/l |

In any experiment, the cultivation was finished at a point in time of 20–40 hours at which glucose was completely consumed. The amount of L-glutamic acid produced and accumulated in the culture liquid was measured. Results are shown in Table 7.

TABLE 7

| Temperature shift timing (hour) | L-Glutamic acid production amount (g/dl) | |
|---|---|---|
| | ATCC 13869 | AJ13029 |
| 8 | 0.5 | 8.3 |
| 12 | 0.1 | 7.0 |
| 16 | 0.0 | 5.4 |
| — | 0.0 | 2.1 |

According to the results, it is understood that AJ13029 strain produces L-glutamic acid in the absence of any biotin action-suppressing agent even in the medium containing an excessive amount of biotin by shifting the cultivation temperature from 31.5° C. to 37° C., and that the amount of L-glutamic acid increases in proportion to the earliness of the shift timing of the cultivation temperature. On the contrary, in the case of ATCC 13869 as the parent strain, little production of L-glutamic acid was observed even by shifting the cultivation temperature.

Bacterial cells were removed by centrifugation from 1 L of cultivation-finished culture liquid having been subjected to the temperature shift 8 hours after the start of cultivation. L-glutamic acid was separated and purified from an obtained supernatant in accordance with an ordinary method using an ion exchange resin. Crystals of obtained sodium L-glutamate were 64.3 g.

2. Investigation on Shift Temperature

Cultivation of *Brevibacterium lactofermentum* ATCC 13869 and AJ13029 was started at 31.5° C. by using a jar fermenter made of glass having a volume of 500 ml in the same manner as the item 1. described above. The cultivation temperature was shifted to 34° C., 37° C. or 39° C., 8 hours after the start of cultivation. A control for comparison was provided in which the cultivation temperature was not shifted to continue cultivation exactly at 31.5° C. In any experiment, the cultivation was finished at a point in time of 20–40 hours at which glucose was completely consumed. The amount of L-glutamic acid produced and accumulated in the culture liquid was measured. Results are shown in Table 8.

TABLE 8

| Temperature after shift (°C.) | L-glutamic acid production amount (g/dl) | |
|---|---|---|
| | ATCC 13869 | AJ13029 |
| 34 | 0.0 | 5.8 |
| 37 | 0.5 | 8.3 |

TABLE 8-continued

| Temperature after shift (°C.) | L-glutamic acid production amount (g/dl) | |
|---|---|---|
| | ATCC 13869 | AJ13029 |
| 39 | 0.9 | 9.2 |
| — | 0.0 | 2.1 |

According to the results, it is understood that there is a tendency that the amount of L-glutamic acid increases as the temperature after the shift becomes high when AJ13029 strain is cultivated and the cultivation temperature is shifted.

EXAMPLE 3

Preparation of Temperature-Sensitive Mutant Strain to Biotin Action-Suppressing Agent Originating from Coryneform L-Glutamic Acid-Producing Bacterium by Genetic Recombination 1. Preparation of Chromosomal DNA of *Brevibacterium lactofermentum* ATCC 13869 (Wild Strain of Coryneform L-Glutamic Acid-Producing Bacterium)

*Brevibacterium lactofermentum* ATCC 13869 was inoculated to 100 ml of T-Y medium (Bacto-tryptone (Difco) 1%, Bacto-yeast extract (Difco) 0.5%, NaCl 0.5% (pH 7.2)), and cultivated at a temperature of 31.5° C. for 8 hours to obtain a culture preparation. The culture preparation was treated by centrifugation at 3,000 r.p.m. for 15 minutes to obtain 0.5 g of wet bacterial cells. Chromosomal DNA was then obtained from the bacterial cells in accordance with a method of Saito and Miura (*Biochem. Biophys. Acta.*, 72, 619 (1963)). Next, 60 μg of the chromosomal DNA and 3 units of a restriction enzyme Sau3AI were respectively mixed with 10 mM Tris-HCl buffer (containing 50 mM NaCl, 10 mM MgSO$_4$, and 1 mM dithiothreitol (pH 7.4)), and reacted at a temperature of 37° C. for 30 minutes. The solution after completion of the reaction was subjected to treatments of phenol extraction and ethanol precipitation in accordance with an ordinary procedure to obtain 50 μg of chromosomal DNA fragments of *Brevibacterium lactofermentum* ATCC 13869 digested with Sau3AI.

2. Construction of Gene Library of *Brevibacterium lactofermentum* ATCC 13869 by Utilizing Plasmid Vector DNA In order to prepare a gene library capable of introduction into cells of both *Escherichia coli* and bacteria belonging to the genus Corynebacterium, a plasmid autonomously replicable in cells of the both was prepared. Specifically, a plasmid pHK4 (Japanese Patent Laid-open No. 5-7491) having a replication origin from an already obtained plasmid pHM1519 (*Agric. Biol. Chem.*, 48, 2901–2903 (1984)) autonomously replicable in coryneform bacteria was digested with restriction enzymes BamHI and KpnI to obtain a gene fragment containing the replication origin. The obtained fragment was blunt-ended by using a DNA blunt end formation kit (produced by Takara Shuzo, Blunting kit), and then inserted into a SalI site of a plasmid vector pHSG399 (produced by Takara Shuzo) by using a SalI linker (produced by Takara Shuzo) to construct pSAC4. *Escherichia coli* HB101 harboring pHK4 has been designated as *Escherichia coli* AJ13136, and deposited on Aug. 1, 1995 in National Institute of Bioscience and Human Technology of Agency of Industrial Science and Technology under a deposition number of FERM BP-5186.

pSAC4 (20 μg) constructed as described above and a restriction enzyme BamHI (20 units) were mixed with 50 mM Tris-HCl buffer (containing 100 mM NaCl and 10 mM magnesium sulfate (pH 7.4)), and reacted at a temperature of 37° C. for 2 hours to obtain a digested solution. The solution was subjected to treatments of phenol extraction and ethanol precipitation in accordance with an ordinary procedure. After that, in order to prevent DNA fragments originating from the plasmid vector from religation, the DNA fragments were dephosphorylated by means of a treatment of bacterial alkaline phosphatase in accordance with a method of *Molecular Cloning 2nd edition* (J. Sambrook, E. F. Fritsch and T. Maniatis, Cold Spring Harbor Laboratory Press, pl. 56 (1989)), followed by treatments of phenol extraction and ethanol precipitation in accordance with an ordinary procedure.

pSAC4 (1 μg) digested with BamHI, the chromosomal DNA fragments (1 μg) of *Brevibacterium lactofermentum* ATCC 13869 digested with Sau3AI having been obtained in the item 1., and T4 DNA ligase (2 units) (produced by Takara Shuzo) were added to 66 mM Tris-HCl buffer (pH 7.5) containing 66 mM magnesium chloride, 10 mM dithiothreitol, and 10 mM ATP, and reacted at a temperature of 16° C. for 16 hours to ligate DNA. Next, the DNA mixture was used to transform *Escherichia coli* DH5 in accordance with an ordinary method, which was spread on an L-agar medium containing 170 μg/ml of chloramphenicol. About 20,000 colonies were obtained. Thus a gene library was constructed.

3. Transformation of *Brevibacterium lactofermentum* AJ11060

Recombinant DNA was recovered from the about 20,000 colonies described above. The recovery was performed in accordance with the method of Saito and Miura described above.

The recombinant DNA mixture was divided into 50 batches which were introduced into the mutant strain AJ11060 having increased surfactant sensitivity in accordance with an ordinary method for transformation by using electric pulses (Japanese Patent Laid-open No. 2-207791). Transformants were inoculated to a glucose-added L-agar medium, and stationarily cultivated at 31.5° C. Thus about 20,000 transformants appeared. These transformants were then replicated on the plate containing 30 mg/l of a surfactant. Several strains, which exhibited resistance to the surfactant and were capable of growth on the aforementioned plate, were obtained from them.

Figure 2:
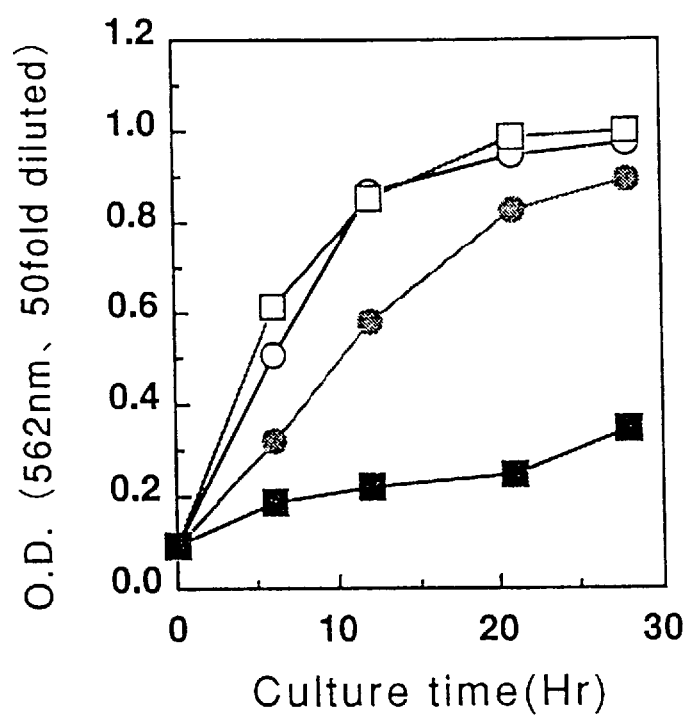
FIG. 2 shows surfactant resistance of Brevibacterium lactofermentum AJ11060 having an introduced plasmid containing dtsR gene.

4. Examination of Surfactant Resistance of Strain Harboring Multiple Copies of dtsR Gene Recombinant DNA was extracted respectively from grown several strains, and AJ11060 strain was retransformed by using the DNA. A strain which exhibited surfactant resistance also in this experiment was obtained. Recombinant DNA harbored by this strain was designated as "pDTR6", and the gene to give surfactant resistance carried by the plasmid was designated as "dtsR". AJ11060 strain into which the plasmid has been introduced was suppressed in growth inhibition in a liquid medium (80 g of glucose, 1 g of KH$_2$PO$_4$, 0.4 g of MgSO$_4$.7H$_2$O, 30 g of (NH$_4$)$_2$SO$_4$, 0.01 g of FeSO$_4$.7H$_2$O, 0.01 g of MnSO$_4$.7H$_2$O, 15 ml of soybean hydrolysate, 200 μg of thiamine hydrochloride, 300 μg of biotin, 4 mg of chloramphenicol, 3.0 g of polyoxyethylene sorbitan monopalmitate and 50 g of CaCO$_3$ in one liter of pure water (the pH of the medium having been adjusted to 8.0 with KOH)) to which 3 g/L of a surfactant was added (FIG. 2).

5. Preparation of Plasmid DNA

The plasmid was prepared in accordance with an ordinary method from AJ11060/pDTR6 containing the recombinant DNA obtained as described above, and introduced into

*Escherichia coli* JM109. Obtained *Escherichia coli* JM109/pDTR6 was preliminarily cultivated at a temperature of 37° C. for 24 hours in 20 ml of a medium comprising tryptone 1%, yeast extract 0.5%, and NaCl 0.5%. An obtained culture liquid (20 ml) was inoculated to a medium (1 l) having the same composition as that described above to perform cultivation at a temperature of 37° C. for 3 hours, followed by addition of chloramphenicol (0.2 g). Cultivation was further performed at the same temperature for 20 hours to obtain a culture liquid. Next, the culture liquid was treated by centrifugation at 3,000 r.p.m. for 10 minutes to obtain each 2 g of wet bacterial cells which were suspended in 350 mM Tris-HCl buffer (20 ml, pH 8.0) containing 25% sucrose. Lysozyme (produced by Sigma) 10 mg, 0.25M EDTA solution (8 ml, pH 8.0), and 20% sodium dodecyl sulfate solution (8 ml) were then respectively added thereto. A temperature-holding treatment was performed at a temperature of 60° C. for 30 minutes to obtain a bacterial lysate solution. A solution of 5M NaCl (13 ml) was added to the bacterial lysate solution to perform a treatment at a temperature of 4° C. for 16 hours, followed by centrifugation at 15,000 r.p.m. for 30 minutes. An obtained supernatant was subjected to treatments of phenol extraction and ethanol precipitation in accordance with an ordinary procedure to precipitate DNA.

The precipitate was dried under a reduced pressure, and then dissolved in 10 mM Tris-HCl buffer (6 ml, pH 7.5) containing 1 mM EDTA. Cesium chloride (6 g) and ethidium bromide (0.2 ml, 19 mg/ml) were added thereto. An equilibrium density-gradient centrifugation was performed at 39,000 r.p.m. for 42 hours by using an ultracentrifuge to isolate DNA. Ethidium bromide was removed by using n-butanol, followed by dialysis against 10 mM Tris-HCl buffer (pH 7.5) containing 1 mM EDTA to obtain about 500 μg of pDTR6 as purified recombinant DNA. A private number of AJ12967 is given to *Escherichia coli* JM109/pDTR6. This strain has been deposited on Feb. 22, 1994 in National Institute of Bioscience and Human Technology of Agency of Industrial Science and Technology under a deposition number of FERM P-14168, transferred to international deposition based on the Budapest Treaty on Feb. 9, 1995, and awarded a deposition number of FERM BP-4994.

6. Analysis of Nucleotide Sequence of DNA Containing dtsR Gene

The nucleotide sequence was determined by using the recombinant DNA obtained in the item 5. The nucleotide sequence was determined in accordance with a method of Sanger by using Taq DyeDeoxy Terminator Cycle Sequencing Kit (produced by Applied Biochemical). The obtained DNA containing the dtsR gene had a nucleotide sequence as shown in SEQ ID NO: 1 in Sequence Listing. The longest open reading frame existing in this sequence was a nucleotide sequence from 359th A to 1987th G in the nucleotide sequence shown in SEQ ID NO: 1. However, it was postulated that 467–469th ATG might be an initiation codon according to analysis of a consensus sequence existing in a region upstream from the gene. An amino acid sequence, which can be encoded by the open reading frame from 359th A to 1987th G, is shown in SEQ ID NO: 1 in Sequence Listing together with its nucleotide sequence. The amino acid sequence is singly shown in SEQ ID NO: 2 in Sequence Listing. A protein encoded by a nucleotide sequence comprising 467–1987th nucleotides was regarded as "DTSR protein".

It is well-known that the methionine residue existing at the N-terminal of a protein is removed by the action of peptidase after translation. This is due to the fact that the methionine at the N-terminal originates from ATG as the translation initiation codon, and thus it often has no relation to an essential function of the protein. It is probable that the removal of methionine residue may occur also in the case of the DTSR protein of the present invention.

The nucleotide sequence and the amino acid sequence were respectively compared with known sequences with respect to their homology. EMBL and SWISS-PROT were used as data bases. As a result, it has been confirmed that the gene shown in SEQ ID NO: 1 in Sequence Listing and the protein encoded by it are novel. However, it has been revealed that there is homology to an already reported protein. This protein is described as β-subunit of propionyl-CoA carboxylase (PPC) protein in *Proc. Natl. Acad. Sci. USA*, vol. 83 (1986) 8049–8053; *Proc. Natl. Acad. Sci. USA*, vol. 83 (1986) 4864–4868; and *Gene*, vol. 122 (1992) 199–202.

7. Preparation of Mutant Type dtsR Gene

The dtsR gene coding for the temperature-sensitive mutant type DTSR protein was obtained in accordance with the following method. pDTR6 plasmid was subjected to a hydroxylamine treatment in vitro in accordance with a method described in a literature, Shortle, D. and Nathans, D., *Proc. Natl. Acad. Sci. U.S.A.*, 75, 270 (1978), and it was introduced into AJ11060 by using the electric pulse method described above. About 20,000 strains of transformants were cultivated on an M-CM2G agar medium at 25° C. for 30 hours to form colonies. The colonies on each plate were replicated on two plates of the medium containing 30 mg/l of a surfactant, followed by cultivation at 31.5° C. and 35° C. for 20 hours. After that, two strains were obtained which grew at 31.5° C. but did not grow at 35° C. Plasmids were extracted from the two strains in accordance with an ordinary method. Thus pDTR6-11 and pDTR6-77 were obtained.

8. Construction of Mutant Type dtsR Gene-Introduced Strains by Gene Substitution Mutant type dtsR gene-substituted strains were obtained in accordance with a homologous recombination method by using a temperature-sensitive plasmid as described in Japanese Patent Laid-open 5–7491. Specifically, pDTR6-11 and pDTR6-77 described above were digested with XbaI and KpnI, and the obtained fragments containing the dtsR gene thereof were ligated with pHSG398 (produced by Takara Shuzo) having been digested with XbaI and KpnI by using the method described above to obtain pHSGX-K-11 and pHSGX-K-77 respectively.

Next, a plasmid pHSC4 (Japanese Patent Laid-open No. 5-7491) having a mutant type replication origin with its temperature-sensitive autonomous replicability obtained from a plasmid autonomously replicable in coryneform bacteria was digested with restriction enzymes BamHI and KpnI to obtain a gene fragment containing the replication origin. The obtained DNA fragment was blunt-ended by using a DNA blunt end formation kit (produced by Takara Shuzo, Blunting kit), and then inserted into KpnI recognition sites of pHSGX-K-11 and pHSGX-K-77 by using a KpnI linker (produced by Takara Shuzo) to construct plasmids pKTCX-K-11 and pKTCX-K-77. *Escherichia coli* AJ12571 harboring pHSC4 has been deposited on Oct. 11, 1990 in National Institute of Bioscience and Human Technology of Agency of Industrial Science and Technology under a deposition number of FERM P-11763, transferred to international deposition based on the Budapest Treaty on Aug. 26, 1991, and deposited under a deposition number of FERM BP-3524.

The two plasmids were respectively introduced into *Brevibacterium lactofermentum* ATCC 13869 by using an electric pulse method, and the dtsR gene on chromosome was substituted into a mutant type in accordance with a method described in Japanese Patent Laid-open No. 5-7491. Specifically, *Brevibacterium lactofermentum* ATCC 13869/pKTCX-K-11 and ATCC 13869/pKTCX-K-77 were cultivated with shaking in an M-CM2G liquid medium at 25° C. for 6 hours, and then spread on an M-CM2G medium containing 5 µg/ml of chloramphenicol. Strains which formed colonies at 34° C. were obtained as plasmid-incorporated strains. Next, strains, which were sensitive to chloramphenicol at 34° C., were obtained from the plasmid-incorporated strains by using a replica method. No. 11 strain and No. 77 strain as strains with lost surfactant resistance at 34° C. were obtained from the sensitive strains. In these strains, the dtsR gene on chromosome is substituted into a mutant type. A DNA fragment obtained by amplifying the region containing the mutant type dtsR gene of the strain No.11 by PCR method using the plasmid pHSGX-K-11 as a template was inserted at HincII recognition site of the plasmid pHSG299 (produced by Takara Shuzo) to obtain a plasmid pHSGDTSR11. *Escherichia coli* JM109 into which the plasmid pHSGDTSR11 was introduced was designated as AJ13137, and deposited on Aug. 1, 1995 in National Institute of Bioscience and Human Technology of Agency of Industrial Science and Technology under a deposition number of FERM BP-5187. The mutant type dtsR gene of the strain No.11 can be obtained by digesting the plasmid pHSGDTSR11 with the restriction enzymes SphI and KpnI.

9. L-Glutamic Acid Productivity of No. 11 Strain and No. 77 Strain

The productivity of L-glutamic acid was evaluated for No. 11 strain and No. 77 strain obtained in the item 8. described above in the same manner as Example 2. Specifically, the same media as those in Example 2 were used, and the cultivation temperature was shifted to 37° C. on the 8th hour after the start of cultivation. As a result, the yield of L-glutamic acid of the strains having the mutant type gene was improved as shown in Table 9.

TABLE 9

| Bacterial strain | L-Glutamic acid (g/dl) |
|---|---|
| ATCC 13869 | 0.5 |
| No. 11 | 7.5 |
| No. 77 | 6.9 |

EXAMPLE 4

Enhancement of Genes of Glutamic Acid Biosynthesis System in Surfactant Temperature-Sensitive Mutant Strain Originating from L-Glutamic Acid-Producing Bacterium 1. Cloning of gdh, qltA and icd Genes gdh (glutamate dehydrogenase gene), gltA (citrate synthase gene), and icd (isocitrate dehydrogenase gene) of *Brevibacterium lactofermentum* were cloned by the PCR method. Primers to be used for the PCR method were synthesized on the basis of already reported sequences of gdh gene (*Molecular Microbiology*, 6(3), 317–326 (1992)), gltA gene (*Microbiology*, 140, 1817–1828 (1994)), and icd gene (*J. Bacteriol.*, 177, 774–782 (1995)) of *Corynebacterium glutamicum*. Oligonucleotides shown in SEQ ID NO: 3 (5' side) and SEQ ID NO: 4 (3' side) in Sequence Listing as primers for amplifying the gdh gene, oligonucleotides shown in SEQ ID NO: 5 (5' side) and SEQ ID NO: 6 (3' side) as primers for amplifying the gltA gene, and oligonucleotides shown in SEQ ID NO: 7 (5' side) and SEQ ID NO: 8 (3' side) as primers for amplifying the icd gene were respectively synthesized and used.

Chromosomal DNA was prepared from *Brevibacterium lactofermentum* ATCC13869 in accordance with the method described in Example 3, which was used as a template to perform PCR by using the aforementioned oligonucleotides as primers. Both ends of obtained amplification products were blunt-ended by using a commercially available DNA blunt end formation kit (produced by Takara Shuzo, Blunting kit), followed by cloning into a SmaI site of a vector plasmid pHSG399 (produced by Takara Shuzo) respectively to obtain plasmids pHSG-gdh, pHSG-gltA, and pHSG-icd.

2. Cloning of ppc Gene

Chromosomal DNA of *Brevibacterium lactofermentum* ATCC13869 was prepared in accordance with the method described in Example 3, which was used as a template to obtain a DNA fragment of about 3.4 Kbp containing ppc gene coding for PEPC (phosphoenolpyruvate carboxylase) by using the PCR method. Primers to be used for the PCR method was synthesized on the basis of an already reported sequence of ppc gene of *Corynebacterium qlutamicum* (*Gene*, 77, 237–251 (1989)). The PCR reaction was conducted in the same manner as described above. Sequences of the primers are shown in SEQ ID NO: 9 (5' side) and SEQ ID NO: 10 (3' side).

An amplification product of the PCR reaction was digested with a restriction enzyme SalI (produced by Takara Shuzo) and inserted at a SalI site of the plasmid pHSG399 to obtain a plasmid pHSG-ppc'. The ppc gene of pHSG-ppc' is inserted in a direction opposite to that of lac promoter of pHSG399.

Next, a promoter of tryptophan operon known as a promoter capable of operation in *Brevibacterium lactofermentum* (*Gene*, 53, 191–200 (1987)) was inserted into a position upstream from the ppc gene on pHSG-ppc'. This promoter is known to exhibit its activity with a sequence comprising 51 nucleotides shown in SEQ ID NO: 11 in Sequence Listing. A nucleotide strand having the sequence shown in SEQ ID NO: 11 and a nucleotide strand having a sequence of SEQ ID NO: 12 as a complementary strand of it were synthesized so as to obtain double-strand DNA containing the 51 base pairs having the promoter activity with both ends coinciding with those of a digested fragment by restriction enzymes KpnI and XbaI.

The both synthesized DNA's were mixed at a concentration of about 10 pmol/µl for each of them, heated at 100° C. for 10 minutes, and then left and cooled at room temperature to achieve annealing. pHSG-ppc' was digested with restriction enzymes KpnI and XbaI (produced by Takara Shuzo), and ligated with the aforementioned promoter. The ligation reaction was performed by using a ligation kit produced by Takara Shuzo. Thus a plasmid pHSG-ppc was obtained in which one copy of the promoter of tryptophan operon was inserted into a position upstream from the ppc gene.

3. Construction of Plasmid Incorporated with Three Types of Genes of gdh, gltA, and icd Three types of the genes of gdh, gltA, and icd were ligated to construct a plasmid. Specifically, the plasmid pHSG-gdh was digested with a restriction enzyme EcoRI, and blunt-ended by using a commercially available DNA blunt end formation kit (produced by Takara Shuzo, Blunting kit), with which the PCR-amplified product of the gltA gene with both ends blunt-ended as described above was ligated to obtain a plasmid pHSG-gdh+gltA. Further, the plasmid pHSG-gdh+gltA was digested with a restriction enzyme KpnI, and blunt-ended in the same manner, with which the PCR-amplified product of the icd gene with both ends blunt-ended as described above was ligated to obtain a plasmid pHSG-gdh+gltA+icd.

4. Construction of Plasmid Incorporated with Three Types of Genes of gdh, gltA, and ppc Three types of the genes of gdh, gltA, and ppc were ligated to construct a plasmid. Specifically, the plasmid pHSG-gdh+gltA was digested with a restriction enzyme KpnI. The plasmid pHSG-ppc was digested with restriction enzymes KpnI and SalI to obtain a ppc gene fragment having the promoter of tryptophan operon at an upstream position. The obtained fragment was blunt-ended by using a DNA blunt end formation kit (produced by Takara Shuzo, Blunting kit), and then inserted into a KpnI site of the plasmid pHSG-gdh+gltA by using a KpnI linker (produced by Takara Shuzo) to obtain a plasmid pHSG-gdh+gltA+ppc.

5. Introduction of Replication Origin for Coryneform Bacterium into the Aforementioned Plasmids In order to make pHSG-gdh, pHSG-gltA, pHSG-ppc, pHSG-icd, pHSG-gdh+gltA+icd, and pHSG-gdh+gltA+ppc autonomously replicable in cells of coryneform bacteria, an already obtained replication origin originating from a plasmid pHM1519 (*Agric. Biol. Chem.*, 48, 2901–2903 (1984)) autonomously replicable in coryneform bacteria was introduced into pHSG-gdh, pHSG-gltA, pHSG-ppc, pHSG-icd, pHSG-gdh+gltA+icd, and pHSG-gdh+gltA+ppc.

Specifically, a plasmid pHK4 (Japanese Patent Laid-open No. 5-7491) having the replication origin from pHM1519 was digested with restriction enzymes BamHI and KpnI to obtain a gene fragment containing the replication origin. The obtained fragment was blunt-ended by using a DNA blunt end formation kit (produced by Takara Shuzo, Blunting kit), and then inserted into a KpnI site of pHSG-gdh, pHSG-gltA, pHSG-ppc, and pHSG-icd respectively by using a KpnI linker (produced by Takara Shuzo) to obtain pGDH, pGLTA, pPPC, and pICD. The replication origin from pHM1519 was inserted into pHSG-gdh+gltA+icd and pHSG-gdh+gltA+ppc respectively at their SalI sites in the same manner by using the SalI linker (produced by Takara Shuzo) to obtain pGDH+GLTA+ICD and pGDH+GLTA+PPC.

6. Confirmation of Expression of Each of Genes Contained in pGDH, pGLTA, pPPC, pICD, pGDH+GLTA+ICD, and pGDH+GLTA+PPC It was confirmed that each of the genes on pGDH, pGLTA, pPPC, pICD, pGDH+GLTA+ICD, and pGDH+GLTA+PPC was expressed in cells of *Brevibacterium lactofermentum*, and that these plasmids fulfilled the function of gene amplification.

Specifically, each of the plasmids was introduced into *Brevibacterium lactofermentum* ATCC 13869 by using an electric pulse method (Japanese Patent Laid-open No. 2-207791). Obtained transformants were selected on a CM2G plate medium containing 4 μg/ml of chloramphenicol (containing polypeptone 10 g, yeast extract 10 g, glucose 5 g, NaCl 5 g, and agar 15 g per 1 L of pure water, pH 7.2). The obtained transformants were cultivated on the CM2G agar medium, inoculated to a medium containing glucose 80 g, $KH_2PO_4$ 1 g, $MgSO_4 \cdot 7H_2O$ 0.4 g, $(NH_4)_2SO_4$ 30 g, $FeSO_4 \cdot 7H_2O$ 0.01 g, $MnSO_4 \cdot 7H_2O$ 0.01 g, soybean hydrolysate solution 15 ml, thiamin hydrochloride 200 μg, biotin 300 μg, and $CaCO_3$ 50 g per 1 L of pure water (with pH adjusted to 8.0 with KOH), and cultivated at 31.5° C. for 16 hours. The culture liquid was centrifuged in accordance with an ordinary method to collect bacterial cells.

Crude extracts obtained by disrupting the bacterial cells were used to measure the GDH (glutamate dehydrogenase) activity of ATCC 13869/pGDH, ATCC 13869/pGDH+GLTA+ICD, and ATCC 13869/pGDH+GLTA+PPC in accordance with a method described in *Molecular Microbiology*, 6(3), 317–326 (1992). As a result, it was found that each of the transformants had the GDH activity which was about 13 times greater than that of ATCC 13869/pSAC4 as a control (Table 10).

The CS (citrate synthase) activity of ATCC 13869/pGLTA, ATCC 13869/pGDH+GLTA+ICD, and ATCC 13869/pGDH+GLTA+PPC was measured in accordance with a method described in *Microbiology*, 140, 1817–1828 (1994). The ICDH (isocitrate dehydrogenase) activity of ATCC 13869/pICD and ATCC 13869/pGDH+GLTA+ICD was measured in accordance with a method described in *J. Bacteriol.*, 177, 774–782 (1995). The PEPC activity of ATCC 13869/pPPC and ATCC 13869/pGDH+GLTA+PPC was measured in accordance with a method described in *Gene*, 77, 237–251 (1989). Measurement results are shown in Tables 11–13. It was found that any transformant had the activity of each of the objective enzymes which was about 2–20 times greater than that of ATCC 13869/pSAC4 as a control. According to this fact, it was confirmed that each of the genes on pGDH, pGLTA, pPPC, pICD, pGDH+GLTA+ICD, and pGDH+GLTA+PPC was expressed in cells of *Brevibacterium lactofermentum*, and fulfilled the function thereof.

TABLE 10

| Bacterial strain | GDH activity (ΔAbs/min/mg protein) |
| --- | --- |
| ATCC 13869/pGDH | 1.36 |
| ATCC 13869/PGDH + GLTA + ICD | 1.28 |
| ATCC 13869/pGDH + GLTA + PPC | 1.33 |
| ATCC 13869/pSAC4 | 0.11 |

TABLE 11

| Bacterial strain | CS activity (μmol/min/mg protein) |
| --- | --- |
| ATCC 13869/pGLTA | 5.5 |
| ATCC 13869/pGDH + GLTA + ICD | 4.8 |
| ATCC 13869/pGDH + GLTA + PPC | 4.8 |
| ATCC 13869/pSAC4 | 0.7 |

TABLE 12

| Bacterial strain | PEPC activity (Units/min/mg protein) |
| --- | --- |
| ATCC 13869/pPPC | 1.12 |
| ATCC 13869/pGDH + GLTA + PPC | 1.04 |
| ATCC 13869/pSAC4 | 0.11 |

TABLE 13

| Bacterial strain | ICDH activity (Units/min/mg protein) |
| --- | --- |
| ATCC 13869/pICD | 3.5 |
| ATCC 13869/pGDH + GLTA + ICD | 2.8 |
| ATCC 13869/pSAC4 | 1.0 |

7. L-Glutamic Acid Production by AJ13029 Strain, and AJ13029 Strains with Amplified gdh, gltA, ppc, and icd Genes A medium (300 ml) containing glucose 60 g, $KH_2PO_4$ 1 g, $MgSO_4 \cdot 7H_2O$ 0.4 g, $(NH_4)_2SO_4$ 30 g, $FeSO_4 \cdot 7H_2O$ 0.01 g, MnSO$_4$.7H$_2$O 0.01 g, soybean hydrolysate solution 15 ml, thiamin hydrochloride 200 μg, and biotin 450 μg per 1 L of pure water was poured into a jar fermenter having a volume of 1 l, and sterilized by heating. Bacterial cells of each of the strains obtained by cultivation on a CM2G agar medium were inoculated thereto, and cultivated at 31.5° C. for 30 hours while controlling pH at 7.0 with ammonia gas.

The bacterial cell density and the amount of L-glutamic acid accumulated in the medium after the cultivation were measured in the same manner as described above. Results are shown in Table 14.

TABLE 14

| Bacterial strain | Plasmid | Cell density (OD) | L-glutamic acid (g/l) |
| --- | --- | --- | --- |
| AJ13029 | — | 0.95 | 33 |
| AJ13029 | pGDH | 1.01 | 35 |
| AJ13029 | pGLTA | 0.93 | 37 |
| AJ13029 | pICD | 0.93 | 37 |
| AJ13029 | pPPC | 0.84 | 38 |
| AJ13029 | pGDH + GLTA + ICD | 1.05 | 39 |
| AJ13029 | pGDH + GLTA + PPC | 0.95 | 41 |
| AJ13029 | pSAC4 | 0.93 | 33 |

EXAMPLE 5

Preparation of Mutant Strains Temperature-Sensitive to Biotin Action-Suppressing Agent from L-Lysin-Producing Strain Originating from Coryneform L-Glutamic Acid-Producing Bacterium 1. Measurement of Sensitivity to Biotin Action-Suppressing Agent of L-Lysine-Producing Strain by Replica Method Sensitivity of an L-lysine-producing strain having AEC resistance, *Brevibacterium lactofermentum* AJ11446 (Japanese Patent Publication No. 62-24073) induced by mutation from *Brevibacterium lactofermentum* ATCC 13869 to polyoxyethylene sorbitan monopalmitate (PESP) was measured as follows in accordance with a replica method.

*Brevibacterium lactofermentum* AJ11446 was cultivated overnight at 31.5° C. on an MCM2G agar plate medium having a composition shown in Table 15 to obtain bacterial cells. They were suspended in sterilized physiological saline, seeded on the aforementioned agar plate medium, and cultivated at 31.5° C. for 20–30 hours to form colonies. They were replicated on an MCM2G agar medium added with each concentration of PESP, and cultivated at 34° C. for 20–30 hours to observe the growth state.

TABLE 15

| Component | Concentration |
| --- | --- |
| Glucose | 0.5% |
| Polypeptone (produced by Nihon Pharmaceutical) | 1.0% |
| Yeast extract (produced by Difco) | 1.0% |
| NaCl | 0.5% |
| DL-methionine | 0.02% |
| Agar | 1.5% | pH 7.2

As a result, it was confirmed that the growth had a threshold value in the vicinity of 3 mg/dl of PESP concentration under this condition as shown in Table 16.

TABLE 16

| PESP concentration (mg/dl) | 0 | 0.1 | 0.3 | 1.0 | 3.0 | 10 | 30 |
| --- | --- | --- | --- | --- | --- | --- | --- |
| Growth | + | + | + | + | + | − | − |

2. Induction of Mutant Strain Exhibiting Temperature Sensitivity to Biotin Action-Suppressing Agent

*Brevibacterium lactofermentum* AJ11446 was cultivated on a bouillon agar medium at 31.5° C. for 24 hours to obtain bacterial cells. The obtained bacterial cells were treated at 30° C. for 30 minutes with an aqueous solution of 250 μg/ml of N-methyl-N'-nitro-N-nitrosoguanidine. A suspension of the bacterial cells at a survival ratio of 1% was then seeded on an MCM2G agar plate medium, and cultivated at 31.5° C. for 20–30 hours to form colonies. They were replicated on an MCM2G agar medium and an MCM2G agar medium added with 3 mg/dl of PESP respectively, and cultivated at 34° C. for 20–30 hours. Bacterial strains were collected, which grew on the MCM2G medium but made no observable growth on the MCM2G medium containing 3 mg/dl of PESP. Thus 250 strains were obtained from about 10,000 colonies. Each of the obtained bacterial strains was reconfirmed for the presence or absence of growth at 34° C. on the MCM2G agar plate medium containing 3 mg/dl of PESP. Strains which apparently exhibited no sensitivity were excluded, and 166 strains which exhibited temperature sensitivity were obtained.

3. Confirmation of Co-Productivity of L-Lysine and L-Glutamic Acid of Mutant Strains Exhibiting Temperature Sensitivity to Biotin Action-Suppressing Agent The productivity of L-lysine and L-glutamic acid was confirmed as follows for the 166 mutant strains obtained in the item 2. described above and their parent strain AJ11446.

AJ11446 strain and each of the mutant strains were cultivated on the MCM2G agar medium at 31.5° C. for 20–30 hours respectively to obtain bacterial cells which were seeded in a liquid medium having a composition shown in Table 17 to start cultivation with shaking at 31.5° C. After 16 hours, the cultivation temperature was shifted to 34° C. to perform cultivation exactly for 48 hours in total. After completion of the cultivation, the presence or absence of L-lysine and L-glutamic acid production was investigated by using thin layer chromatography. As a result, it was confirmed that 31 strains among the 166 mutant strains simultaneously produced the two amino acids. When the 31 strains were cultivated at 31.5° C. for 48 hours without shifting the cultivation temperature, co-production of L-lysine and L-glutamic acid was observed with respect to 3 strains.

TABLE 17

| Component | Concentration |
| --- | --- |
| Glucose | 10 g/dl |
| KH$_2$PO$_4$ | 0.1 g/dl |
| MgSO$_4$ · 7H$_2$O | 0.04 g/dl |
| FeSO$_4$ · 7H$_2$O | 0.001 g/dl |
| MnSO$_4$ · 4H$_2$O | 0.001 g/dl |
| (NH$_4$)$_2$SO$_4$ | 2 g/dl |
| Soybean protein hydrolysate solution | 3 ml/dl |
| DL-alanine | 0.35 g/dl |
| Nicotinic acid amide | 5 mg/l |
| Thiamin hydrochloride | 0.2 mg/l |
| Biotin | 0.3 mg/l |

TABLE 17-continued

| Component | Concentration |
| --- | --- |
| Antifoaming agent | 0.05 ml/l |
| CaCO₃ | 5 g/dl | pH 7.0

Accumulation amounts of L-lysine and L-glutamic acid are shown in Table 18 for representative strains of the mutant strains and AJ11446 strain.

TABLE 18

| Bacterial strain | Temperature shift | Lys (g/dl) | Glu (g/dl) |
| --- | --- | --- | --- |
| AJ11446 | yes | 2.09 | 0.00 |
|  | no | 2.41 | 0.00 |
| EK-015 | yes | 2.17 | 0.70 |
|  | no | 2.35 | 0.00 |
| EK-036 | yes | 2.35 | 0.34 |
|  | no | 2.20 | 0.14 |
| EK-100 | yes | 1.69 | 0.93 |
|  | no | 1.71 | 0.47 |
| EK-112 | yes | 1.96 | 0.69 |
|  | no | 2.50 | 0.00 |
| EK-117 | yes | 0.99 | 1.88 |
|  | no | 1.70 | 0.00 |

4. Confirmation of Temperature Sensitivity to Biotin Action-Suppressing Agent

Temperature sensitivity to PESP of the bacteria for simultaneously producing L-lysine and L-glutamic acid obtained in the item 3. described above was confirmed as follows by means of liquid culture.

Each of the mutant strains and their parent strain were cultivated on the MCM2G agar plate medium at 31.5° C. for 24 hours to obtain bacterial cells. The obtained bacterial cells were inoculated to an MCM2G liquid medium and an MCM2G liquid medium containing PESP at a concentration of 1 mg/dl to perform cultivation with shaking at 31.5° C. and 34° C. for 24 hours. Optical densities (O.D.) of obtained culture liquids were measured at 660 nm. The relative growth degree in the PESP-added medium was determined provided that growth in the medium without addition of PESP was regarded as 100. Results are shown in Table 19.

TABLE 19

|  | Relative growth degree | |
| --- | --- | --- |
| Bacterial strain | 31.5° C. | 34° C. |
| AJ11446 | 95 | 90 |
| EK-015 | 90 | 27 |
| EK-036 | 84 | 45 |
| EK-100 | 87 | 22 |
| EK-112 | 98 | 36 |
| EK-117 | 84 | 47 |

As shown in this table, each of the mutant strains had a relative growth degree of 80 or more at 31.5° C., but 50 or less at 34° C. in the presence of 1 mg/dl of PESP, clearly having sensitivity to PESP.

Figure 3:
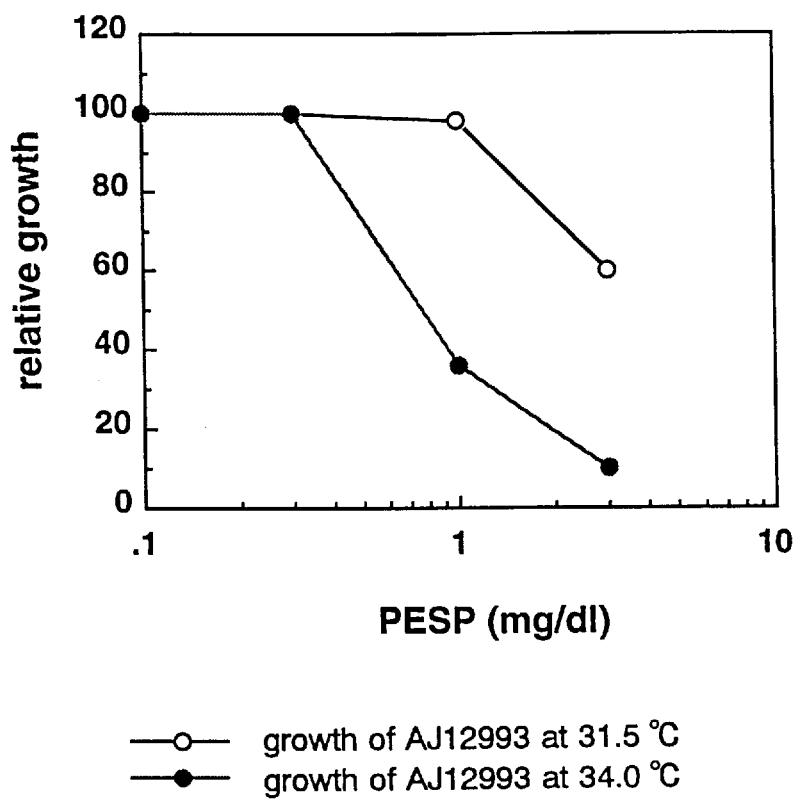
FIG. 3 shows influences exerted by PESP on growth of Brevibacterium lactofermentum AJ12993 at 31.5° C. and 34° C.

Influences exerted by PESP on growth at 31.5° C. and 34° C. are shown in FIG. 3 for EK-112 among the mutant strains obtained in the item 3. described above. Growth approximately equivalent to that in the absence of PESP was observed in the presence of PESP at a concentration of not more than 1 mg/dl at 31.5° C. However, growth in the presence of 1 mg/dl of PESP was remarkably inhibited at 34° C. as compared with growth in the absence of PESP.

Thus it is demonstrated that this mutant strain has temperature sensitivity.

Among the mutant strains, EK-112 has been designated as *Brevibacterium lactofermentum* AJ12993, deposited on Jun. 3, 1994 in National Institute of Bioscience and Human Technology of Agency of Industrial Science and Technology under a deposition number of FERM P-14348, transferred to international deposition based on the Budapest Treaty on Aug. 1, 1995, and awarded a deposition number of FERM BP-5188.

EXAMPLE 6

Production of L-Lysine and L-Glutamic Acid by Co-fermentation

1. Investigation on Cultivation Temperature Shift Timing

*Brevibacterium lactofermentum* AJ11446 or AJ12993 was inoculated to the seed culture medium having the composition shown in Table 6 described above, and cultivated with shaking at 31.5° C. for 24 hours to obtain a seed culture. The medium for full-scale cultivation having the composition shown in Table 6 was dispensed into each amount of 300 ml and poured into a jar fermenter made of glass having a volume of 500 ml, and sterilized by heating. After that, 40 ml of the seed culture was inoculated thereto. Cultivation was started by using an agitation speed of 800–1,300 rpm, an aeration amount of 1/2–1/1 vvm, and a cultivation temperature of 31.5° C. The culture liquid was maintained to have pH of 7.5 by using ammonia gas. The cultivation temperature was shifted to 34° C., 8, 12 or 16 hours after the start of cultivation. A control for comparison was provided in which the cultivation temperature was not shifted, and cultivation was continued exactly at 31.5° C.

In any experiment, the cultivation was finished at a point in time of 40–50 hours at which glucose was completely consumed. The amounts of L-lysine and L-glutamic acid produced and accumulated in the culture liquid were measured. Results are shown in Table 20.

TABLE 20

|  | AJ11446 | | AJ12993 | |
| --- | --- | --- | --- | --- |
| Temperature shift timing (hour) | Lys (g/dl) | Glu (g/dl) | Lys (g/dl) | Glu (g/dl) |
| 8 | 5.4 | 0.0 | 4.4 | 1.8 |
| 12 | 5.5 | 0.0 | 4.5 | 1.6 |
| 16 | 5.6 | 0.0 | 4.7 | 1.2 |
| — | 5.9 | 0.0 | 6.0 | 0.0 |

According to the results, it is understood that AJ12993 strain produces both L-lysine and L-glutamic acid in the absence of any biotin action-suppressing agent even in the medium containing an excessive amount of biotin by shifting the cultivation temperature from 31.5° C. to 34° C., that the rate of L-glutamic acid increases in proportion to the earliness of the shift timing of the cultivation temperature, and that the rate of L-lysine increases in proportion to the lateness thereof. On the contrary, in the case of AJ11446 strain as the parent strain, only L-lysine was produced, and production of L-glutamic acid was not observed even by shifting the cultivation temperature.

Bacterial cells were removed by centrifugation from 1 l of cultivation-finished culture liquid having been subjected to the temperature shift 8 hours after the start of cultivation. L-lysine and L-glutamic acid were separated and purified from an obtained supernatant in accordance with an ordinary method using ion exchange resins. Crystals of obtained L-lysine hydrochloride were 31.7 g, and crystals of obtained sodium L-glutamate were 13.9 g.

2. Investigation on Shift Temperature

Cultivation of *Brevibacterium lactofermentum* AJ11446 and AJ12993 was started at 31.5° C. by using a jar fermenter made of glass having a volume of 500 ml in the same manner as the item 1. described above. The cultivation temperature was shifted to 33° C., 34° C. or 35° C., 8 hours after the start of cultivation. A control for comparison was provided in which the cultivation temperature was not shifted to continue cultivation exactly at 31.5° C. In any experiment, the cultivation was finished after 40–50 hours had passed. The amounts of L-lysine and L-glutamic acid produced and accumulated in the culture liquid were measured. Results are shown in Table 21.

TABLE 21

| Temperature after shift (°C.) | AJ11446 | | AJ12993 | |
|---|---|---|---|---|
| | Lys (g/dl) | Glu (g/dl) | Lys (g/dl) | Glu (g/dl) |
| 33 | 5.6 | 0.0 | 4.9 | 1.1 |
| 34 | 5.4 | 0.0 | 4.4 | 1.8 |
| 35 | 5.2 | 0.0 | 3.8 | 2.1 |
| — | 5.9 | 0.0 | 6.0 | 0.0 |

According to the results, it is understood that there is a tendency that the rate of L-glutamic acid increases as the temperature after the shift becomes high, and the rate of L-lysine increases as it becomes low when AJ12993 strain is cultivated and the cultivation temperature is shifted.

INDUSTRIAL APPLICABILITY to the invention, the temperature sensitivity to the biotin action-suppressing agent is given to the coryneform L-glutamic acid-producing bacteria. Thus L-glutamate can be produced inexpensively and stably by fermentation even when a material containing an excessive amount of biotin is used as a carbon source.

Further, the L-lysine productivity is given. Thus L-lysine and L-glutamate can be simultaneously produced inexpensively and stably by fermentation even when a material containing an excessive amount of biotin is used as a carbon source.

What is claimed is:

1. A method of producing L-glutamic acid by fermentation without biotin-action suppressive agents, comprising the steps of:

cultivating a mutant strain in a liquid medium;

raising the temperature at an intermediate stage of the cultivation to a temperature where said mutant strain is sensitive to a biotin action-suppressing agent at a concentration at which growth of said mutant strain at 31.5° C. is approximately equivalent to that in the absence of said biotin action-suppressing agent;

producing and accumulating L-glutamic acid in the medium; and collecting L-glutamic acid from the medium, said mutant strain being a coryneform L-glutamic acid-producing bacterium, having a temperature-sensitive mutation with respect to a biotin action-suppressing agent produced by applying a mutation treatment to a coryneform L-glutamic acid-producing bacterium, conducting a replication method in a growth medium containing a biotin-action-suppressing agent and selecting a strain which is temperature sensitive at 37° C. in said growth medium but not temperature sensitive in media without said biotin-action-suppressing agent, and having the ability to produce L-glutamic acid in the absence of any biotin action-suppressing agent in a medium containing an excessive amount of biotin.

2. A method of producing L-glutamic acid according to claim 1, wherein the biotin action-suppressing agent is polyoxyethylene sorbitan monopalmitate.

3. A method of producing L-glutamic acid according to claim 1, wherein protein expression levels in said mutant strain of one or more genes selected from the group consisting of glutamate dehydrogenase gene, citrate synthase gene, phosphoenolpyruvate dehydrogenase gene and isocitrate dehydrogenase gene have been enhanced.

4. A method of producing L-lysine and L-glutamic acid by fermentation without biotin-action suppressing agents, comprising the steps of:

cultivating a mutant strain in a liquid medium;

raising the temperature at an intermediate stage of the cultivation to a temperature where said mutant strain is sensitive to a biotin action-suppressing agent at a concentration at which growth of said mutant strain at 31.5° C. is approximately equivalent to that in the absence of said biotin action-suppressing agent;

producing and accumulating L-lysine and L-glutamic acid in the medium; and collecting them from the medium, said mutant strain being a coryneform L-glutamic acid-producing bacterium, having a mutation to give L-lysine productivity and a temperature-sensitive mutation with respect to a biotin action-suppressing agent produced by applying a mutation treatment to a coryneform L-glutamic acid-producing bsacterium, conducting a replication method in a growth medium containing a biotin-action-suppressing agent and selecting a strain which is temperature sensitive at 37° C. in said growth medium but not temperature sensitive in media without said biotin-action-suppressing agent, and having the ability to produce L-lysine and L-glutamic acid in the absence of any biotin action-suppressing agent in a medium containing an excessive amount of biotin.

5. A method of producing L-lysine and L-glutamic acid according to claim 4, wherein the biotin action-suppressing agent is polyoxyethylene sorbitan monopalmitate.

6. A mutant strain of coryneform bacteria, having a temperature-sensitive mutation with respect to a biotin action-suppressing agent produced by applying a mutation treatment to a coryneform L-glutamic acid-producing bacterium conducting a replication method in a growth medium containing a biotin-action-suppressing agent and selecting a strain which is temperature sensitive at about 37° C. in said growth medium but not temperature sensitive in media without said biotin-action-suppressing agent, and having the ability to produce L-glutamic acid in the absence of any biotin action-suppressing agent in a medium containing an excessive amount of biotin.

7. A mutant strain according to claim 6, wherein the biotin action-suppressing agent is polyoxyethylene sorbitan monopalmitate.

8. A mutant strain according to claim 6 having a mutation to give L-lysine productivity and having the ability to produce both L-lysine and L-glutamic acid in the absence of any biotin action-suppressing agent in a medium containing an excessive amount of biotin.

9. A mutant strain according to claim 8, wherein the biotin action-suppressing agent is polyoxyethylene sorbitan monopalmitate.

10. A method of breeding mutant coryneform strains having the ability to produce L-glutamic acid in the absence of any biotin action-suppressing agent in a medium containing an excessive amount of biotin, comprising:

giving temperature sensitivity with respect to a biotin action-suppressing agent to a coryneform L-glutamic acid-producing bacterium produced by applying a mutation treatment to a coryneform L-glutamic acid-producing bsacterium, conducting a replication method in a growth medium containing a biotin-action-suppressing agent and selecting a strain which is temperature sensitive at 37° C. in said growth medium but not temperature sensitive in media without said biotin-action-suppressing agent.

11. A method of breeding mutant coryneform strains having the ability to produce both L-lysine and L-glutamic acid in the absence of any biotin action-suppressing agent in a medium containing an excessive amount of biotin, comprising:

giving temperature sensitivity with respect to a biotin action-suppressing agent produced by applying a mutation treatment to a coryneform L-glutamic acid-producing bsacterium, conducting a replication method in a growth medium containing a biotin-action-suppressing agent and selecting a strain which is temperature sensitive at about 37° C. in said growth medium but not temperature sensitive in media without said biotin-action-suppressing agent and giving L-lysine productivity to a coryneform L-glutamic acid-producing bacterium.

12. A method of producing L-glutamic acid according to claim 1, wherein the temperature is raised to about 33°–40° C. at said intermediate stage of the cultivation.

13. A method of producing L-glutamic acid according to claim 1, wherein the temperature is raised to about 37°–40° C. at said intermediate stage of the cultivation.

14. A method of producing L-lysine and L-glutamic acid according to claim 4, wherein the temperature is raised to about 33°–40° C. at said intermediate stage of the cultivation.

15. A method of producing L-lysine and L-glutamic acid according to claim 4, wherein the temperature is raised to about 37°–40° C. at said intermediate stage of the cultivation.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 2855 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Brevibacterium lactofermentum
        ( B ) STRAIN: ATCC13869

( i x ) FEATURE:
        ( A ) NAME/KEY: CDS
        ( B ) LOCATION: 359..1987

( x i ) SEQUENCE DESCRIPTION: SEQ ID NO: 1:

```
GATCTTGGAA   CTCGACAGTT   TTCACCGTCC   AGTTTGGAGC   GCCTGAGCTT   GCAAGCTCCA        60

GCAAGTCAGC   ATTAGTGGAG   CCTGTCACTT   TTTCGTAAAT   GACCTGGCCA   AAGTCACCGT       120

TTTGGAGCAA   TTTTTCCTTC   AGGAGCTCAA   CGTTTAGCGG   CTCTCTGGAT   CGTGAAATGT       180

CAACGTTCAT   GGAAGCCAAT   GTAGTGGGGT   CGCGTCGAAA   AGCGCGCTTT   AAGGGCGACA       240

CGCCCAAAAA   GTTTTACCTT   TAAAAACTAC   CCGCACGCAG   CACGAACCTG   TTCAGTGATG       300
```

-continued

```
TAAATCACCG CGGAAATATT GTGGACGTTA CCCCCGCCTA CCGCTACGAT TTCAAAAC            358

ATG ACC ATT TCC TCA CCT TTG ATT GAC GTC GCC AAC CTT CCA GAC ATC            406
Met Thr Ile Ser Ser Pro Leu Ile Asp Val Ala Asn Leu Pro Asp Ile
 1           5                  10                  15

AAC ACC ACT GCC GGC AAG ATC GCC GAC CTT AAG GCT CGC CGC GCG GAA            454
Asn Thr Thr Ala Gly Lys Ile Ala Asp Leu Lys Ala Arg Arg Ala Glu
             20                  25                  30

GCC CAT TTC CCC ATG GGT GAA AAG GCA GTA GAG AAG GTC CAC GCT GCT            502
Ala His Phe Pro Met Gly Glu Lys Ala Val Glu Lys Val His Ala Ala
         35                  40                  45

GGA CGC CTC ACT GCC CGT GAG CGC TTG GAT TAC TTA CTC GAT GAG GGC            550
Gly Arg Leu Thr Ala Arg Glu Arg Leu Asp Tyr Leu Leu Asp Glu Gly
     50                  55                  60

TCC TTC ATC GAG ACC GAT CAG CTG GCT CGC CAC CGC ACC ACC GCT TTC            598
Ser Phe Ile Glu Thr Asp Gln Leu Ala Arg His Arg Thr Thr Ala Phe
 65                  70                  75                  80

GGC CTG GGC GCT AAG CGT CCT GCA ACC GAC GGC ATC GTG ACC GGC TGG            646
Gly Leu Gly Ala Lys Arg Pro Ala Thr Asp Gly Ile Val Thr Gly Trp
                 85                  90                  95

GGC ACC ATT GAT GGA CGC GAA GTC TGC ATC TTC TCG CAG GAC GGC ACC            694
Gly Thr Ile Asp Gly Arg Glu Val Cys Ile Phe Ser Gln Asp Gly Thr
             100                 105                 110

GTA TTC GGT GGC GCG CTT GGT GAG GTG TAC GGC GAA AAG ATG ATC AAG            742
Val Phe Gly Gly Ala Leu Gly Glu Val Tyr Gly Glu Lys Met Ile Lys
         115                 120                 125

ATC ATG GAG CTG GCA ATC GAC ACC GGC CGC CCA TTG ATC GGT CTT TAC            790
Ile Met Glu Leu Ala Ile Asp Thr Gly Arg Pro Leu Ile Gly Leu Tyr
     130                 135                 140

GAA GGC GCT GGC GCT CGC ATT CAG GAC GGC GCT GTC TCC CTG GAC TTC            838
Glu Gly Ala Gly Ala Arg Ile Gln Asp Gly Ala Val Ser Leu Asp Phe
145                 150                 155                 160

ATT TCC CAG ACC TTC TAC CAA AAC ATT CAG GCT TCT GGC GTT ATC CCA            886
Ile Ser Gln Thr Phe Tyr Gln Asn Ile Gln Ala Ser Gly Val Ile Pro
                165                 170                 175

CAG ATC TCC GTC ATC ATG GGC GCA TGT GCA GGT GGC AAC GCT TAC GGC            934
Gln Ile Ser Val Ile Met Gly Ala Cys Ala Gly Gly Asn Ala Tyr Gly
            180                 185                 190

CCA GCC CTG ACC GAC TTC GTG GTC ATG GTG GAC AAG ACC TCC AAG ATG            982
Pro Ala Leu Thr Asp Phe Val Val Met Val Asp Lys Thr Ser Lys Met
        195                 200                 205

TTC GTT ACC GGC CCA GAC GTG ATC AAG ACC GTC ACC GGC GAG GAA ATC           1030
Phe Val Thr Gly Pro Asp Val Ile Lys Thr Val Thr Gly Glu Glu Ile
    210                 215                 220

ACC CAG GAA GAG CTT GGC GGA GCA ACC ACC CAC ATG GTG ACC GCT GGC           1078
Thr Gln Glu Glu Leu Gly Gly Ala Thr Thr His Met Val Thr Ala Gly
225                 230                 235                 240

AAC TCC CAC TAC ACC GCT GCG ACC GAT GAG GAA GCA CTG GAT TGG GTA           1126
Asn Ser His Tyr Thr Ala Ala Thr Asp Glu Glu Ala Leu Asp Trp Val
                245                 250                 255

CAG GAC CTG GTG TCC TTC CTC CCA TCC AAC AAT CGC TCT TAC ACA CCA           1174
Gln Asp Leu Val Ser Phe Leu Pro Ser Asn Asn Arg Ser Tyr Thr Pro
            260                 265                 270

CTG GAA GAC TTC GAC GAG GAA GAA GGC GGT GTT GAA GAA AAC ATC ACC           1222
Leu Glu Asp Phe Asp Glu Glu Glu Gly Gly Val Glu Glu Asn Ile Thr
        275                 280                 285

GCT GAC GAT CTG AAG CTC GAC GAG ATC ATC CCA GAT TCC GCG ACC GTT           1270
Ala Asp Asp Leu Lys Leu Asp Glu Ile Ile Pro Asp Ser Ala Thr Val
    290                 295                 300

CCT TAC GAC GTC CGC GAT GTC ATC GAA TGC CTC ACC GAC GAT GGC GAA           1318
Pro Tyr Asp Val Arg Asp Val Ile Glu Cys Leu Thr Asp Asp Gly Glu
```

```
305                      310                      315                      320
TAC CTG GAA ATC CAG GCA GAC CGC GCA GAA AAC GTT GTT ATT GCA TTC    1366
Tyr Leu Glu Ile Gln Ala Asp Arg Ala Glu Asn Val Val Ile Ala Phe
                325                      330                  335

GGC CGC ATC GAA GGC CAG TCC GTT GGA TTT GTT GCC AAC CAG CCA ACC    1414
Gly Arg Ile Glu Gly Gln Ser Val Gly Phe Val Ala Asn Gln Pro Thr
                340                  345                  350

CAG TTC GCT GGC TGC CTG GAC ATC GAC TCC TCT GAG AAG GCA GCT CGC    1462
Gln Phe Ala Gly Cys Leu Asp Ile Asp Ser Ser Glu Lys Ala Ala Arg
            355                  360                  365

TTC GTC CGC ACC TGC GAC GCG TTT AAC ATC CCA ATC GTC ATG CTT GTC    1510
Phe Val Arg Thr Cys Asp Ala Phe Asn Ile Pro Ile Val Met Leu Val
        370                  375                  380

GAC GTC CCC GGC TTC CTT CCA GGC GCA GGC CAG GAG TAT GGT GGC ATC    1558
Asp Val Pro Gly Phe Leu Pro Gly Ala Gly Gln Glu Tyr Gly Gly Ile
385                  390                  395                  400

CTG CGT CGT GGC GCA AAG CTG CTC TAC GCA TAC GGC GAA GCA ACC GTT    1606
Leu Arg Arg Gly Ala Lys Leu Leu Tyr Ala Tyr Gly Glu Ala Thr Val
                405                  410                  415

CCA AAG ATT ACC GTC ACC ATG CGT AAG GCT TAC GGC GGA GCG TAC TGC    1654
Pro Lys Ile Thr Val Thr Met Arg Lys Ala Tyr Gly Gly Ala Tyr Cys
                420                  425                  430

GTG ATG GGT TCC AAG GGC TTG GGC TCT GAC ATC AAC CTT GCA TGG CCA    1702
Val Met Gly Ser Lys Gly Leu Gly Ser Asp Ile Asn Leu Ala Trp Pro
            435                  440                  445

ACC GCA CAG ATC GCC GTC ATG GGC GCT GCT GGC GCA GTC GGA TTC ATC    1750
Thr Ala Gln Ile Ala Val Met Gly Ala Ala Gly Ala Val Gly Phe Ile
        450                  455                  460

TAC CGC AAG GAG CTC ATG GCA GCT GAT GCC AAG GGC CTC GAT ACC GTA    1798
Tyr Arg Lys Glu Leu Met Ala Ala Asp Ala Lys Gly Leu Asp Thr Val
465                  470                  475                  480

GCT CTG GCT AAG TCC TTC GAG CGC GAG TAC GAA GAC CAC ATG CTC AAC    1846
Ala Leu Ala Lys Ser Phe Glu Arg Glu Tyr Glu Asp His Met Leu Asn
                485                  490                  495

CCG TAC CAC GCT GCA GAA CGT GGC CTG ATC GAC GGC GTG ATC CTG CCA    1894
Pro Tyr His Ala Ala Glu Arg Gly Leu Ile Asp Ala Val Ile Leu Pro
                500                  505                  510

AGC GAA ACC CGC GGA CAG ATT TCC CGC AAC CTT CGC CTG CTC AAG CAC    1942
Ser Glu Thr Arg Gly Gln Ile Ser Arg Asn Leu Arg Leu Leu Lys His
            515                  520                  525

AAG AAC GTC ACT CGC CCT GCT CGC AAG CAC GGC AAC ATG CCA CTG        1987
Lys Asn Val Thr Arg Pro Ala Arg Lys His Gly Asn Met Pro Leu
        530                  535                  540

TAAATCGGCG AATCCATAAA GGTTCAAAAG AATTCAATAA GGATTCGATA AGGGTTCGAT  2047

AAGGGTTCGA TAAGGGCCGA CTTAAATGAT TGGATGTAAA GAAATACCAA TGAAAATTGG  2107

CAACTCTTTA CACCCAATCT TTAAGACATG GGGGGTGGCG CTGGGCTAAT ATAACCGGTT  2167

AGCGAAACGA TTAGTCCCTT GTTAGGGGGA TTAACCCTCG AAGTGGGTCG TATTTTGGCG  2227

TTTGTATGTT CACACAAGAA CCCTGCACAA CGCCTTCAAA GTACGTCGAC CACGACCAAG  2287

CGCATTATTC ACTCTCACCC TTCAGGATTT AGACTAAGAA ACCATGACTG CAGCACAGAC  2347

CAAACCTGAC CTCACCACCA CGGCTGGAAA GCTGTCCGAT CTTCGCTCCC GTCTTGCAGA  2407

AGCTCAAGCT CCAATGGGCG AAGCAACTGT AGAAAAAGTG CACGCTGCTG GCAGGAAGAC  2467

TGCCCGCGAA CGTATCGAGT ATTTGCTCGA TGGGCTCT TTCGTAGAGA TCGATGCTCT    2527

TGCTCGTCAC CGTTCCAAGA ACTTCGGCCT GGATGCCAAG CGTCCAGCTA CTGACGGTGT  2587

TGTGACTGGT TACGGCACCA TCGATGGCCG TAAGGTCTGT GTGTTCTCCC AGGACGGCGC  2647
```

```
TGTATTCGGT GGCGCTTTGG GTGAAGTTTA TGGTGAAAAG ATCGTTAAGG TTATGGATCT    2707

TGCGATCAAG ACCGGTGTGC CTTTGATCGG AATCAATGAG GGTGCTGGTG CGCGTATCCA    2767

GGAAGGTGTT GTGTCTCTGG GTCTGTACTC ACAGATTTTC TACCGCAACA CCCAGGCGTC    2827

TGGCGTTATC CCACAGATCT CTTTGATC                                      2855
```

(2) INFORMATION FOR SEQ ID NO: 2:

(i) SEQUENCE CHARACTERISTICS:
        (A) LENGTH: 543 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Thr Ile Ser Ser Pro Leu Ile Asp Val Ala Asn Leu Pro Asp Ile
  1               5                  10                  15

Asn Thr Thr Ala Gly Lys Ile Ala Asp Leu Lys Ala Arg Arg Ala Glu
             20                  25                  30

Ala His Phe Pro Met Gly Glu Lys Ala Val Glu Lys Val His Ala Ala
         35                  40                  45

Gly Arg Leu Thr Ala Arg Glu Arg Leu Asp Tyr Leu Leu Asp Glu Gly
     50                  55                  60

Ser Phe Ile Glu Thr Asp Gln Leu Ala Arg His Arg Thr Thr Ala Phe
 65                  70                  75                  80

Gly Leu Gly Ala Lys Arg Pro Ala Thr Asp Gly Ile Val Thr Gly Trp
                 85                  90                  95

Gly Thr Ile Asp Gly Arg Glu Val Cys Ile Phe Ser Gln Asp Gly Thr
                100                 105                 110

Val Phe Gly Gly Ala Leu Gly Glu Val Tyr Gly Glu Lys Met Ile Lys
            115                 120                 125

Ile Met Glu Leu Ala Ile Asp Thr Gly Arg Pro Leu Ile Gly Leu Tyr
        130                 135                 140

Glu Gly Ala Gly Ala Arg Ile Gln Asp Gly Ala Val Ser Leu Asp Phe
145                 150                 155                 160

Ile Ser Gln Thr Phe Tyr Gln Asn Ile Gln Ala Ser Gly Val Ile Pro
                165                 170                 175

Gln Ile Ser Val Ile Met Gly Ala Cys Ala Gly Gly Asn Ala Tyr Gly
            180                 185                 190

Pro Ala Leu Thr Asp Phe Val Met Val Asp Lys Thr Ser Lys Met
        195                 200                 205

Phe Val Thr Gly Pro Asp Val Ile Lys Thr Val Thr Gly Glu Glu Ile
    210                 215                 220

Thr Gln Glu Glu Leu Gly Gly Ala Thr Thr His Met Val Thr Ala Gly
225                 230                 235                 240

Asn Ser His Tyr Thr Ala Ala Thr Asp Glu Ala Leu Asp Trp Val
                245                 250                 255

Gln Asp Leu Val Ser Phe Leu Pro Ser Asn Asn Arg Ser Tyr Thr Pro
            260                 265                 270

Leu Glu Asp Phe Asp Glu Glu Gly Gly Val Glu Glu Asn Ile Thr
        275                 280                 285

Ala Asp Asp Leu Lys Leu Asp Glu Ile Ile Pro Asp Ser Ala Thr Val
        290                 295                 300

Pro Tyr Asp Val Arg Asp Val Ile Glu Cys Leu Thr Asp Asp Gly Glu
305                 310                 315                 320
```

Tyr Leu Glu Ile Gln Ala Asp Arg Ala Glu Asn Val Val Ile Ala Phe
            325                 330             335

Gly Arg Ile Glu Gly Gln Ser Val Gly Phe Val Ala Asn Gln Pro Thr
            340                 345             350

Gln Phe Ala Gly Cys Leu Asp Ile Asp Ser Ser Glu Lys Ala Ala Arg
            355                 360             365

Phe Val Arg Thr Cys Asp Ala Phe Asn Ile Pro Ile Val Met Leu Val
370                     375             380

Asp Val Pro Gly Phe Leu Pro Gly Ala Gly Gln Glu Tyr Gly Gly Ile
385                 390             395                     400

Leu Arg Arg Gly Ala Lys Leu Leu Tyr Ala Tyr Gly Glu Ala Thr Val
                405             410             415

Pro Lys Ile Thr Val Thr Met Arg Lys Ala Tyr Gly Gly Ala Tyr Cys
            420                 425             430

Val Met Gly Ser Lys Gly Leu Gly Ser Asp Ile Asn Leu Ala Trp Pro
        435             440             445

Thr Ala Gln Ile Ala Val Met Gly Ala Ala Gly Ala Val Gly Phe Ile
    450             455             460

Tyr Arg Lys Glu Leu Met Ala Ala Asp Ala Lys Gly Leu Asp Thr Val
465                 470             475                     480

Ala Leu Ala Lys Ser Phe Glu Arg Glu Tyr Glu Asp His Met Leu Asn
            485                 490             495

Pro Tyr His Ala Ala Glu Arg Gly Leu Ile Asp Ala Val Ile Leu Pro
            500             505             510

Ser Glu Thr Arg Gly Gln Ile Ser Arg Asn Leu Arg Leu Leu Lys His
        515             520             525

Lys Asn Val Thr Arg Pro Ala Arg Lys His Gly Asn Met Pro Leu
530                     535             540

( 2 ) INFORMATION FOR SEQ ID NO: 3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( x i ) SEQUENCE DESCRIPTION: SEQ ID NO: 3:

GCTAGCCTCG GGAGCTCTAG                    20

( 2 ) INFORMATION FOR SEQ ID NO: 4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( i i i ) HYPOTHETICAL: NO ( i v ) ANTI-SENSE: YES ( x i ) SEQUENCE DESCRIPTION: SEQ ID NO: 4:

GATCTTTCCC AGACTCTGGC                                                                                       20

( 2 ) INFORMATION FOR SEQ ID NO: 5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( i i i ) HYPOTHETICAL: NO ( i v ) ANTI-SENSE: NO ( x i ) SEQUENCE DESCRIPTION: SEQ ID NO: 5:

TAATGCCACC GACACCCACC                                                                                       20

( 2 ) INFORMATION FOR SEQ ID NO: 6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( i i i ) HYPOTHETICAL: NO ( i v ) ANTI-SENSE: YES ( x i ) SEQUENCE DESCRIPTION: SEQ ID NO: 6:

TCAACGCCCA CATAGTGGAC                                                                                       20

( 2 ) INFORMATION FOR SEQ ID NO: 7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( i i i ) HYPOTHETICAL: NO ( i v ) ANTI-SENSE: NO ( x i ) SEQUENCE DESCRIPTION: SEQ ID NO: 7:

GAATTCGCTC CCGGTGACGC                                                                                       20

( 2 ) INFORMATION FOR SEQ ID NO: 8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( i i i ) HYPOTHETICAL: NO ( i v ) ANTI-SENSE: YES ( x i ) SEQUENCE DESCRIPTION: SEQ ID NO: 8:

GATGCAGAAT TCCTTGTCGG                                                          20

( 2 ) INFORMATION FOR SEQ ID NO: 9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( i i i ) HYPOTHETICAL: NO ( i v ) ANTI-SENSE: NO ( x i ) SEQUENCE DESCRIPTION: SEQ ID NO: 9:

GTCGACGGCG GACTTGTCGG                                                          20

( 2 ) INFORMATION FOR SEQ ID NO: 10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( i i i ) HYPOTHETICAL: NO ( i v ) ANTI-SENSE: YES ( x i ) SEQUENCE DESCRIPTION: SEQ ID NO: 10:

GTCGACAAAA CCCAAAAAAA                                                          20

( 2 ) INFORMATION FOR SEQ ID NO: 11:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( i i i ) HYPOTHETICAL: NO ( i v ) ANTI-SENSE: NO ( x i ) SEQUENCE DESCRIPTION: SEQ ID NO: 11:

CTGCGGAAAC TACACAAGAA CCCAAAAATG ATTAATAATT GAGACAAGCT T                       51

( 2 ) INFORMATION FOR SEQ ID NO: 12:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: other..syntetic DNA ( i i i ) HYPOTHETICAL: NO -continued ( i v ) ANTI-SENSE: YES ( x i ) SEQUENCE DESCRIPTION: SEQ ID NO: 12:

CTAGAAGCTT GTCTCAATTA TTAATCATTT TTGGGTTCTT GTGTAGTTTC CGCAGGTAC    59